United States Patent
Gunatillake et al.

(10) Patent No.: US 12,129,331 B2
(45) Date of Patent: Oct. 29, 2024

(54) POLYURETHANE/UREA MATERIALS

(71) Applicant: Foldax, Inc., Salt Lake City, UT (US)

(72) Inventors: Pathiraja A. Gunatillake, Mulgrave (AU); Mark Bown, Notting Hill (AU); Raju Adhikari, Glen Waverley (AU)

(73) Assignee: Foldax, Inc., Salt Lake City, UT (US)

( * ) Notice: Subject to any disclaimer, the term of this patent is extended or adjusted under 35 U.S.C. 154(b) by 68 days.

(21) Appl. No.: 17/364,033

(22) Filed: Jun. 30, 2021

(65) Prior Publication Data

US 2022/0119580 A1 Apr. 21, 2022

Related U.S. Application Data

(63) Continuation of application No. 15/771,719, filed as application No. PCT/AU2016/051019 on Oct. 28, 2016, now Pat. No. 11,053,342.

(30) Foreign Application Priority Data

Oct. 29, 2015 (AU) ................. 2015904428

(51) Int. Cl.
| | |
|---|---|
| C08G 18/61 | (2006.01) |
| A61F 2/24 | (2006.01) |
| A61L 27/18 | (2006.01) |
| C08G 18/48 | (2006.01) |
| C08G 18/76 | (2006.01) |
| C08G 77/458 | (2006.01) |
| C08G 77/46 | (2006.01) |
| C08G 81/02 | (2006.01) |
| C08L 83/12 | (2006.01) |

(52) U.S. Cl.
CPC ............ *C08G 18/61* (2013.01); *A61F 2/2409* (2013.01); *A61L 27/18* (2013.01); *C08G 18/7671* (2013.01); *C08G 77/458* (2013.01); *C08G 77/46* (2013.01); *C08G 81/025* (2013.01); *C08G 81/027* (2013.01); *C08L 83/12* (2013.01); *A61F 2210/0071* (2013.01); *A61F 2240/00* (2013.01); *A61L 2430/20* (2013.01); *C08L 2203/02* (2013.01); *C08L 2207/04* (2013.01)

(58) Field of Classification Search
None
See application file for complete search history.

(56) References Cited

U.S. PATENT DOCUMENTS

| 4,382,144 A | 5/1983 | Rosenberg et al. |
| 6,313,254 B1 | 11/2001 | Meijs et al. |
| 7,026,423 B2 | 4/2006 | Gunatillake et al. |
| 8,759,467 B2 | 6/2014 | Taniguchi et al. |
| 10,266,657 B2 | 4/2019 | Gunatillake et al. |
| 10,723,844 B2 | 7/2020 | Gunatillake et al. |
| 11,053,342 B2 | 7/2021 | Gunatillake et al. |
| 2002/0028901 A1 | 3/2002 | Gunatillake et al. |
| 2007/0027285 A1 | 2/2007 | Gunatillake et al. |
| 2009/0182111 A1* | 7/2009 | Padsalgikar ............ A61L 31/06 528/28 |
| 2011/0086940 A1 | 4/2011 | Rega |
| 2011/0190905 A1 | 8/2011 | Behan |
| 2011/0207897 A1 | 8/2011 | Mccrba et al. |
| 2011/0237740 A1 | 9/2011 | Iyer et al. |
| 2012/0010302 A1 | 1/2012 | Hartung et al. |
| 2015/0320555 A1 | 11/2015 | Beith |
| 2016/0122477 A1 | 5/2016 | Rhee et al. |
| 2017/0119923 A1 | 5/2017 | Gunatillake et al. |
| 2018/0346654 A1 | 12/2018 | Gunatillake et al. |
| 2019/0284343 A1 | 9/2019 | Gunatillake et al. |

FOREIGN PATENT DOCUMENTS

| AU | 2000/39472 | | 11/2000 |
| CA | 2367678 A1 * | | 11/2000 |
| CN | 1299382 A | | 6/2001 |
| CN | 1352664 A | | 6/2002 |
| EP | 2404950 A1 | | 1/2012 |
| EP | 2495270 A1 | | 9/2012 |
| JP | 2005/263988 A | | 9/2005 |
| WO | WO-1998/13405 A1 | | 4/1998 |
| WO | WO-00/64971 A1 | | 11/2000 |
| WO | WO 2005/052019 A1 * | | 6/2005 |
| WO | WO-2006/002045 A2 | | 1/2006 |
| WO | WO-2009/081681 A1 | | 7/2009 |
| WO | WO-2014/151485 A1 | | 9/2014 |

(Continued)

OTHER PUBLICATIONS

"Hydrodynamic Function of Polyurethane Prosthetic Heart Valves; Influences of Young's Modulus and Leaflet Thickness" authored by Bernacca et al. and published in Biomaterials (2002) 23, 45-50.*
Barszczewska-Rybarek et al., "Study of the Effects of Urethane-Dimethacrylates Structure on the Morphology and Properties of Polymers Based on Them," Polimery, 53(3): 190-194 (2008).
Dandeniyage et al., "Development of High Strength Siloxane Poly(Urenthane-Urea) Elastomers Based on Linked Macrodiols for Heart Valve Application," BioMed Mater Res Part B, (2017).
Ekin et al., "Synthesis and Characterization of Novel Carbamate Linked Di- and Tetra-Functional Poly(Dimethylsiloxane) Oligomers and Their Block Copolymers With Poly(?-Caprolactone) Using Combinatorial and High-Throughput Methods," Polymer Preprints, 47(2): 1204-1205 (2006).
Ekin et al., "Synthesis, formulation, and characterization of siloxane-polyurethane coatings for underwater marine applications using combinatorial high-throughput experimentation," J. Coat. Technol. Res., 4(4): 435-451 (2007).

(Continued)

*Primary Examiner* — Marc S Zimmer
(74) *Attorney, Agent, or Firm* — Foley Hoag LLP; Janine S. Ladislaw; David S. Surry

(57) ABSTRACT

The present disclosure provides soft block copolymer segments of Formula 1 for thermoplastic polyurethane or polyurethaneurea elastomer materials and their reaction products with divalent compounds, such as diisocyanates, chain extenders and optional additional polyols or polyamines. Also disclosed herein are methods for the production of the soft block copolymer segments, and possible applications of these materials in the formation of biomaterials for articles including medical devices such as implants, heart valves and drug delivery devices.

20 Claims, 1 Drawing Sheet

(56) References Cited

FOREIGN PATENT DOCUMENTS

| WO | WO-2015/082397 A1 | 6/2015 |
| WO | WO-2017070743 A1 | 5/2017 |

OTHER PUBLICATIONS

Extended European Search Report for EP Application No. 20209436.3 dated Jun. 22, 2021.

Extended European Search Report issued by the European Patent Office in corresponding Application No. PCT/AU2016051019 issued Apr. 24, 2019.

Fang et al., "Microphase Separated Structures and Properties of PDMS-MDI-PEG Copolymer Surface," Chinese Journal of Polymer Science, 27(3): 327-334 (2009).

International Search Report and Written Opinion for International Application No. PCT/AU/2016/051019 dated Jan. 3, 2017.

Kozakiewicz et al., "Water-Cured Poly(Urethane-Urea)s Containing Soft Segments Originating From Siloxane/ Carbonate Macrodiols," Polimery, 57: 791-798 (2012).

Laskovenko et al., "Synthesis of Block Oligodimethylsiloxane-Oligoether Urethane Diols," Russian Journal of Applied Chemistry, 69(11): 1732-1734 (1996).

Simmons et al., "Long-Term in Vivo Biostability of Poly(Dimethylsiloxane)/ Poly(Hexamethylene Oxide) Mixed Macrodiol-based Polyurethane Elastomers," Graduate School of Biomedical Engineering, University of New South Wales Sydney, 25: 4887-4900 (2004).

Smetankina et al., "Carbofunctional Organosilicon Compounds. XII Synthesis of Siloxane-Urethane Oligomers with Terminal Isocyanate and Hydroxyl Groups," Sintez I Fiziko-Chimiya Polimerov, 8: 34-36 (1971).

* cited by examiner

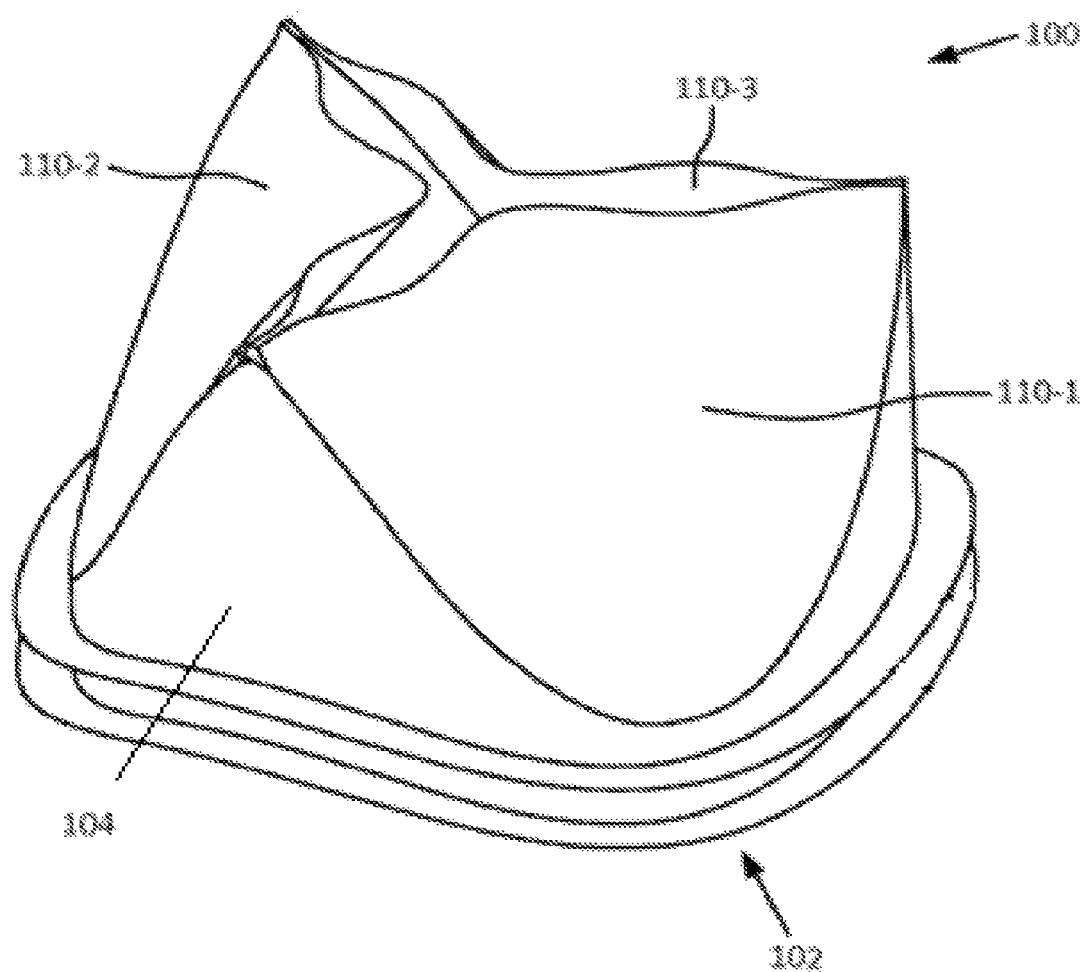

POLYURETHANE/UREA MATERIALS

CROSS-REFERENCE TO RELATED APPLICATIONS

The present application is a continuation of U.S. patent application Ser. No. 15/771,719, filed Apr. 27, 2018, which is the National Stage of International Application Serial No. PCT/AU2016/051019, filed Oct. 28, 2016, which claims priority from Australian Provisional Patent Application No. 2015904428, filed on 29 Oct. 2015, the entire contents of each of which are incorporated herein by reference in their entireties.

TECHNICAL FIELD

The present disclosure relates to soft block copolymer segments for a thermoplastic polyurethane or polyurethaneurea elastomer material and their reaction products with divalent compounds, such as diisocyanates, chain extenders and optional additional polyols or polyamines. Also disclosed are methods for the preparation of the soft block copolymer segments and reaction products, and the use of these components in the manufacture of materials such as biomaterials for articles, including medical devices such as implants.

BACKGROUND

Previously, polyurethanes based on two or more macrodiols which are chemically different have been reported. This has been achieved by using a mixture or a blend of the macrodiols for making the polyurethane, and employing either a one-step or a two-step polymerisation procedure. This approach has a number of disadvantages including:
- where the macrodiols are not miscible, the resulting polyurethane is compositionally heterogeneous;
- only a limited number of macrodiol combinations can be used to make polyurethanes with good mechanical properties, and the segments from each of the macrodiols are randomly distributed within the polyurethane chain (often resulting in polyurethanes with poor mechanical properties); and
- the incorporation of higher molecular weight macrodiols or macrodiamines are limited to polyols such as polyethers, polyesters or polycarbonates.

There is a need for identifying alternative block copolymers for use in polyurethane or polyurethaneurea elastomer materials in order to prepare various polymer products exhibiting a broad range of mechanical properties. The alternative block copolymers may address one or more disadvantages of previous approaches.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

The present disclosure relates to macrodiols and macrodiamines which are chemically linked (linked-macrodiols or macrodiamines) to contain one or more chemically distinct moieties within a polymeric backbone. These macrodiols and macrodiamines may be useful in formulating polyurethanes/ureas for biomedical and non-biomedical applications.

In a first aspect, there is provided a block copolymer segment of Formula 1 for a thermoplastic polyurethane or polyurethaneurea elastomer material:

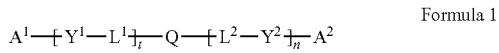

Formula 1 wherein
$A^1$ is an endcapping group;
$A^2$ is hydrogen or an endcapping group;
each $Y^1$ and $Y^2$ are independently selected from a polysiloxane macrodiol, polysiloxane macrodiamine, polyether macrodiol, polycarbonate macrodiol, polyester macrodiol, and a polyhydrocarbon macrodiol;
each $L^1$ and $L^2$ is a divalent linking group independently selected from urethane, urea carbonate, amide, ester, and phosphonate;
n is an integer of 1 to 5;
t is an integer of 0 to 5; and
Q is selected from a moiety of Formula A or Formula B:

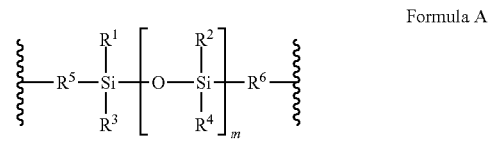

Formula A wherein
$R^1$, $R^2$, $R^3$, and $R^4$, are each independently selected from hydrogen and an optionally substituted straight chain, branched or cyclic, saturated and unsaturated hydrocarbon radical;
$R^5$ and $R^6$ are each independently selected from a straight chain, branched or cyclic, saturated and unsaturated hydrocarbon radical optionally interrupted with one or more heteroatoms independently selected from O, N and S;
m is an integer of 1 to 50; or

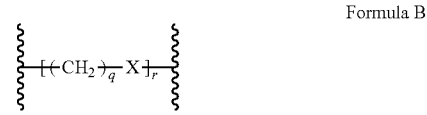

Formula B wherein
X is a group selected from OC(O)O, C(O)O and O;
q is an integer of 1 to 50; and
r is an integer of 2 to 50.

In a second aspect, there is provided a thermoplastic polyurethane or polyurethaneurea elastomer material comprising a plurality of soft segments and hard segments, wherein the plurality of soft segments are each derived from at least one block copolymer segment of Formula 1 according to the first aspect, or any embodiments thereof described herein, and optionally an additional polyol or polyamine.

In a third aspect, there is provided a thermoplastic polyurethane or polyurethaneurea elastomer material comprising a reaction product of:

i. at least one block copolymer segment of Formula 1 according to the first aspect, or any embodiments thereof described herein;
ii. a diisocyanate;
iii. one or more chain extenders; and
iv. optionally an additional polyol or polyamine.

In a fourth aspect, there is provided an article which is composed wholly or partly of the polyurethane or polyurethaneurea elastomeric material according to the second or third aspect, or any embodiments thereof described herein.

In a fifth aspect, there is provided an article which is a medical device which is composed wholly or partly of the polyurethane or polyurethaneurea elastomeric material according to the second or third aspect, or any embodiments thereof described herein.

In a sixth aspect, there is provided process for preparing the block copolymer segment of Formula 1 according to the first aspect, or any embodiments thereof described herein, whereby the process comprises the step of combining:
i. at least one macrodiol; or
ii. at least one macrodiamine; or
iii. a mixture of at least one macrodiol and at least one macrodiamine, with a divalent linking compound.

In a seventh aspect, there is provided a process for preparing a thermoplastic polyurethane or polyurethaneurea elastomer comprising the silicon based block copolymer segment of Formula 1 according to the first aspect, or any embodiments thereof described herein, whereby the process comprises the steps of:
i. providing a block copolymer segment of Formula 1 according to the first aspect, or any embodiments thereof described herein, or preparing a block copolymer segment of Formula 1 using the process according to the sixth aspect, or any embodiments thereof described herein;
ii. optionally reacting the composition of step i. with a divalent compound and: at least one macrodiol; at least one macrodiamine; or a mixture of at least one macrodiol and at least one macrodiamine; and
iii. reacting the block copolymer segment of step i. or step ii. with a chain extender or a mixture of chain extenders to form the polyurethane or polyurethaneurea elastomer.

BRIEF DESCRIPTION OF THE DRAWINGS

FIG. 1 is a perspective view of an example embodiment of a prosthetic heart valve incorporating polymers disclosed herein.

DESCRIPTION OF EMBODIMENTS

The present disclosure describes the following various non-limiting embodiments, which relate to investigations undertaken to identify alternative block copolymer segments for use in polyurethane/urea materials and polymer products thereof.

It was surprisingly found that the block copolymer segments disclosed herein can provide a number of advantages including enhanced soft segment properties in polyurethane/urea thermoplastic polymers. Enhanced soft segment properties include an improved miscibility with hard segments and increased inter molecular hydrogen bonding.

According to at least some embodiments described herein, the block copolymers, polyurethane/urea materials and polymer products thereof can provide advantages including:

allowing a wide range of macrodiols, including those that are not miscible with each other, to be linked to produce a raft of different linked macrodiols which act as "macro-monomers";

the formulation of polyurethanes with low modulus, high elasticity and high tear strength for use in cardio vascular medical implants;

by utilising certain linker molecules, the synthesis of the linked-macrodiol can be prepared prior to the polyurethane/polyurethaneurea synthesis, without involving any purification steps; and the ability to increase the molecular weight of a "macro-monomer" by linking two or more macrodiols or diamine molecules, allows for the formulation of materials with a wide range of mechanical properties, via the variation in the relative proportions of 'soft' segments (for example a segment derived from the macrodiol or macrodiamine), and hard segments (for example a segment derived from the diisocyanate and an optional chain extender).

Terms

With regards to the definitions provided herein, unless stated otherwise, or implicit from context, the defined terms and phrases include the provided meanings. Unless explicitly stated otherwise, or apparent from context, the terms and phrases below do not exclude the meaning that the term or phrase has acquired by a person skilled in the relevant art. The definitions are provided to aid in describing particular embodiments, and are not intended to limit the claimed invention, because the scope of the invention is limited only by the claims. Furthermore, unless otherwise required by context, singular terms shall include pluralities and plural terms shall include the singular.

Herein, the term "polyurethane" relates to a polymer chain that comprises urethane (carbamate, —NH—COO—) links which connect monomer or "macro-monomer" units. Polyurethanes can be produced via the reaction of molecules containing a minimum of two isocyanate functional groups with other molecules which contain at least two alcohol (hydroxyl) groups.

Herein, the term "polyureas" relates to a polymer chain that comprises urea links (—NH—CO—NH—) which connect monomer or "macro-monomer" units. Polyureas can be produced via the reaction of molecules containing a minimum of two isocyanate groups with other molecules which contain at least two amine groups.

Herein, the term "polyurethaneurea" relates to a polymer chain that comprises both urethane and urea linking groups.

Herein, the term "macrodiol" refers to a polymeric material comprising two hydroxyl groups. For example, a block copolymer segment of Formula 1 with two hydroxyl groups.

Herein, the term "macrodiamine" refers to a polymeric material comprising two amine groups. For example, a block copolymer segment of Formula 1 with two amine groups.

Herein, the term "polyhydrocarbon macrodiol" refers to a polymeric material with a polymer backbone consisting entirely of hydrogen and carbon, and two hydroxyl groups. Examples include, but are not limited to: poly(isobutylene)diol, poly(butadiene)diol and hydrogenated poly(butadiene diol).

The term "macro-monomer" refers to a polymeric substance that possesses at least one polymerisable group, for example a hydroxyl group, which is capable of reacting with another compound, for example a diisocyanate.

Throughout the present specification, various aspects and components of the invention can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial numbers (except where integers are required), within the recited range, for example, 1, 2, 3, 4, 5, 5.5 and 6. This applies regardless of the breadth of the disclosed range. Where specific values are required, these will be indicated in the specification.

Herein, the term "hydrocarbon radical" refers to an optionally substituted straight chain, branched or cyclic, saturated and unsaturated hydrocarbon radicals. The hydrocarbon radicals (for example for substituents $R^1$, $R^2$, $R^3$, $R^4$, $R^5$, $R^6$, $R^7$, $R^8$, $R^9$, $R^{10}$, $R^{11}$ and/or $R^{12}$) includes optionally substituted alkyl, alkenyl, alkynyl, aryl or heterocyclyl radicals.

The term "alkyl" denotes straight chain, branched or mono- or poly-cyclic alkyl, for example $C_{1-18}$alkyls or $C_{3-8}$cycloalkyls. "$C_{1-18}$ alkyls" and "$C_{3-8}$cycloalkyls" refer to alkyl groups having 1 to 18 carbon atoms or cycloalkyl groups having 3 to 8 carbon atoms.

As understood by a person skilled in the art, the term "$C_{1-18}$alkyls" means alkyl groups with 1, 2, 3, 4, 5, 6, 7, 8, 9, 10, 11, 12, 13, 14, 15, 16, 17 or 18 carbon atoms or a range comprising any of two of those integers and including: 1-2, 1-3, 1-4, 1-5, 1-6, 1-7, 1-8, 1-9, 1-10, 1-11, 1-12, 1-13, 1-14, 1-15, 1-16, 1-17, or 1-18 carbon atoms. Examples of straight chain and branched alkyl groups include optionally substituted: methyl, ethyl, propyl, isopropyl, butyl, isobutyl, sec-butyl, amyl, isoamyl, sec-amyl, 1,2-dimethylpropyl, 1,1-dimethylpropyl, pentyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, or 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl and 1,1,3,3-tetramethylbutyl groups, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- or 8-methylnonyl, 1-, 2-, 3-, 4-, 5- or 6-ethyloctyl, 1-, 2-, 3-, or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1,2-pentylheptyl, tridecyl, tetradecyl, pentadecyl, hexadecyl, heptadecyl, or octadecyl groups.

As understood by a person skilled in the art, the term "$C_{3-8}$cycloalkyls" means cycloalkyl groups with 3, 4, 5, 6, 7 or 8 carbon atoms or a range comprising any of two of those integers and including 3-4, 3-5, 3-6, 3-7, 3-8, 4-5, 4-6, 4-7, 4-8, 5-6, 5-7, 5-8, 6-7, 6-8 or 7-8 carbon atoms. Examples of cyclic alkyl groups include optionally substituted: cyclopropyl, cyclobutyl, cyclopentyl, cyclohexyl, cycloheptyl or cyclooctyl groups.

The term "alkenyl" relates to groups formed from straight chain, branched or mono- or poly-cyclic alkenes including ethylenically mono- or poly-unsaturated alkyl or cycloalkyl groups as defined above, for example $C_{2-18}$ alkenyls or $C_{3-8}$ cycloalkenyls. "$C_{2-18}$ alkenyls" or "$C_{3-8}$ cycloalkenyls" refer to alkenyl or cycloalkenyl groups having 2 to 18 carbon atoms or 3 to 8 carbon atoms, respectively.

As understood by a person skilled in the art, the term "$C_{2-18}$alkenyls" means alkenyl groups with 2, 3, 4, 5, 6, 7, 8, 9, 10, 11, 12, 13, 14, 15, 16, 17 or 18 carbon atoms or a range comprising any of two of those integers and including: 2-3, 2-4, 2-5, 2-6, 2-7, 2-8, 2-9, 2-10, 2-11, 2-12, 2-13, 2-14, 2-15, 2-16, 2-17, or 2-18 carbon atoms. As understood by a person skilled in the art, the term "$C_{3-8}$ cycloalkenyls" means cycloalkenyl groups with 3, 4, 5, 6, 7 or 8 carbon atoms or a range comprising any of two of those integers and including 3-4, 3-5, 3-6, 3-7, 3-8, 4-5, 4-6, 4-7, 4-8, 5-6, 5-7, 5-8, 6-7, 6-8 or 7-8 carbon atoms. Examples of alkenyl and cycloalkenyl groups include optionally substituted: vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl groups.

The term "alkynyl" denotes groups formed from straight chain, branched, or mono- or poly-cyclic alkynes, for example $C_{2-18}$alkynyls or $C_{3-8}$cycloalkynyls. Examples of alkynyl groups include optionally substituted: ethynyl, 1-propynyl, 1 and 2-butynyl, 2-methyl-2-propynyl, 2-pentynyl, 3-pentynyl, 4-pentynyl, 2-hexynyl, 3-hexynyl, 4-hexynyl, 5-hexynyl groups, 10-undecynyl, 4-ethyl-1-octyn-3-yl, 7-dodecynyl, 9-dodecynyl, 10-dodecynyl, 3-methyl-2-dodecyn-3-yl, 2-tridecynyl, 11-tridecynyl, 3-tetradecynyl, 7-hexadecynyl and 3-octadecynyl.

The term "aryl" denotes single, polynuclear, conjugated and fused residues of aromatic hydrocarbons. Examples of aryl groups include optionally substituted: phenyl, biphenyl, terphenyl, quaterphenyl, phenoxyphenyl, naphthyl, tetrahydronaphthyl, anthracenyl, dihydroanthracenyl, benzanthracenyl, dibenzanthracenyl and phenanthrenyl groups.

The term "heterocyclyl" denotes mono- or poly-cyclic heterocyclyl groups containing at least one heteroatom selected from nitrogen, sulphur and oxygen. Suitable heterocyclyl groups include optionally substituted: N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl; saturated 3 to 6-membered heterononocyclic groups containing 1 to 4 nitrogen atoms, such as pyrrolidinyl, imidazolidinyl, piperidino or piperazinyl; unsaturated condensed heterocyclic groups containing 1 to 5 nitrogen atoms, such as, indolyl, isoindolyl, indolizinyl, benzimidazolyl, quinolyl, isoquinolyl, indazolyl, benzotriazolyl or tetrazolopyridazinyl; unsaturated 3 to 6-membered heteromonocyclic group containing an oxygen atom, such as, pyranyl or furyl; unsaturated 3 to 6-membered hetermonocyclic group containing 1 to 2 sulphur atoms, such as, thienyl; unsaturated 3 to 6-membered heteromonocyclic group containing 1 to 2 oxygen atoms and 1 to 3 nitrogen atoms, such as, oxazolyl, isoazolyl or oxadiazolyl; saturated 3 to 6-membered heteromonocyclic group containing 1 to 2 oxygen atoms and 1 to 3 nitrogen atoms, such as, morpholinyl; unsaturated condensed heterocyclic group containing 1 to 2 oxygen atoms and 1 to 3 nitrogen atoms, such as, benzoxazolyl or benzoxadiazolyl; unsaturated 3 to 6-membered heteromonocyclic group containing 1 to 2 sulphur atoms and 1 to 3 nitrogen atoms, such as thiazolyl or thiadiazolyl; saturated 3 to 6-membered heteromonocyclic group containing 1 to 2 sulphur atoms and 1 to 3 nitrogen atoms, such as, thiadiazolyl; and unsaturated condensed heterocyclic group containing 1 to 2 sulphur atoms and 1 to 3 nitrogen atoms, such as benzothiazolyl or benzothiadiazolyl groups.

Herein, "optionally substituted" means that a group may or may not be further substituted with one or more groups selected from: oxygen, nitrogen, sulphur, alkyl, alkenyl, alkynyl, aryl, halo, haloalkyl, haloalkenyl, haloalkynyl, haloaryl, hydroxy, alkoxy, alkenyloxy, alkynyloxy, aryloxy, carboxy, benzyloxy, haloalkoxy, haloalkenyloxy, haloalkynyloxy, haloaryloxy, nitro, nitroalkyl, nitroalkenyl, nitroalkynyl, nitroaryl, nitroheterocyclyl, azido, amino, alkylamino, alkenylamino, alkynylamino, arylamino, benzylamino, acyl, alkenylacyl, alkynylacyl, arylacyl, acylamino, acyloxy, aldehydo, alkylsulphonyl, arylsulphonyl, alkylsulphonylamino, arylsulphonylamino, alkylsulphonyloxy, arylsulphonyloxy, heterocyclyl, heterocycloxy, heterocyclylamino, haloheterocyclyl, alkylsulphenyl, arylsulphenyl, carboalkoxy, carboaryloxy, mercapto, alkylthio, arylthio, or acylthio groups. It will be appreciated that the term "optionally substituted" may also be referred to as "substituted or unsubstituted".

Block Copolymer Segments

Disclosed herein are block copolymer segments of Formula 1 for a thermoplastic polyurethane or polyurethaneurea elastomer material:

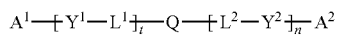

Formula 1 wherein
$A^1$ is an endcapping group;
$A^2$ is hydrogen or an endcapping group;
each $Y^1$ and $Y^2$ are independently selected from a polysiloxane macrodiol, polysiloxane macrodiamine, polyether macrodiol, polycarbonate macrodiol, polyester macrodiol, and a polyhydrocarbon macrodiol;
each $L^1$ and $L^2$ is a divalent linking group independently selected from urethane, urea carbonate, amide, ester, and phosphonate;
n is an integer of 1 to 5;
t is an integer of 0 to 5; and
Q is selected from a moiety of Formula A or Formula B:

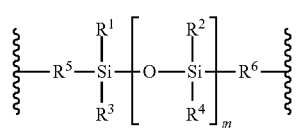

Formula A wherein
$R^1$, $R^2$, $R^3$, and $R^4$, are each independently selected from hydrogen and an optionally substituted straight chain, branched or cyclic, saturated and unsaturated hydrocarbon radical;
$R^5$ and $R^6$ are each independently selected from a straight chain, branched or cyclic, saturated and unsaturated hydrocarbon radical optionally interrupted with one or more heteroatoms independently selected from O, N and S;
m is an integer of 1 to 50; or

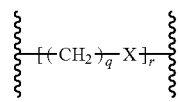

Formula B wherein
X is a group selected from OC(O)O, C(O)O and O;
q is an integer of 1 to 50; and
r is an integer of 2 to 50.

The block copolymer segment may be a block copolymer segment of Formula 1A

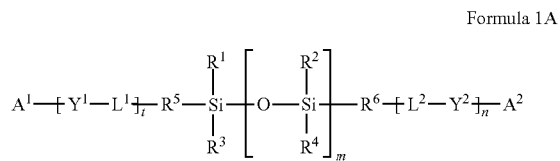

Formula 1A wherein each $A^1$, $A^2$, $Y^1$, $L^1$, $L^2$, $Y^2$, $R^1$, $R^2$, $R^3$, $R^4$, $R^5$, $R^6$, m, n and t, are as defined herein.

The block copolymer segment may be a block copolymer segment of Formula 1A(i):

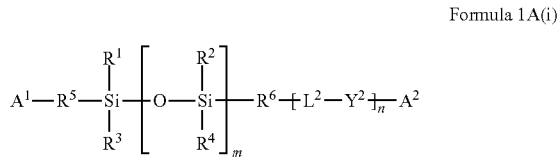

Formula 1A(i)

wherein each $A^1$, $A^2$, $L^2$, $Y^2$, $R^1$, $R^2$, $R^3$, $R^4$, $R^5$, $R^6$, m and n, are as defined herein.

The block copolymer segment may be a block copolymer segment of Formula 1A(i)(a):

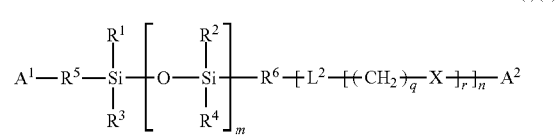

Formula 1A(i)(a)

wherein each $A^1$, $A^2$, $L^2$, $R^1$, $R^2$, $R^3$, $R^4$, $R^5$, $R^6$, X, m, q and r, are as defined herein.

The block copolymer segment may be a block copolymer segment of Formula 1A(i)(b):

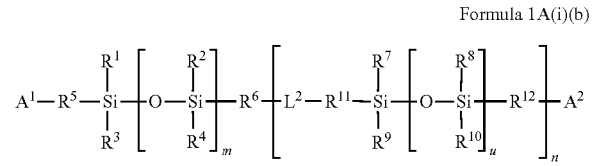

Formula 1A(i)(b)

wherein each $A^1$, $A^2$, $L^2$, $R^1$, $R^2$, $R^3$, $R^4$, $R^5$, $R^6$, $R^7$, $R^8$, $R^9$, $R^{10}$, $R^{11}$, $R^{12}$, m, n and u, are as defined herein.

The block copolymer segment may be a block copolymer segment of Formula 1A(ii):

Formula 1A(ii)
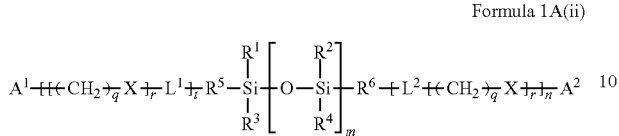

wherein each $A^1$, $A^2$, $L^1$, $L^2$, $R^1$, $R^2$, $R^3$, $R^4$, $R^5$, $R^6$, X, m, q, r and t, are as defined herein.

The block copolymer segment may be a block copolymer segment of Formula 1B:

Formula 1B
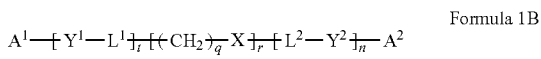

wherein each $A^1$, $A^2$, $Y^1$, $L^1$, $L^2$, $Y^2$, X, n, q, r and t are as defined herein.

The block copolymer segment may be a block copolymer segment of Formula 1B(i):

Formula 1B(i)
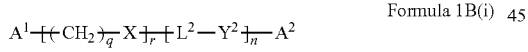

wherein each $A^1$, $A^2$, $L^2$, $Y^2$, X, n, q and r are as defined herein.

The block copolymer segment may be a block copolymer segment of Formula 1B(i)(a):

Formula 1B(i)(a)
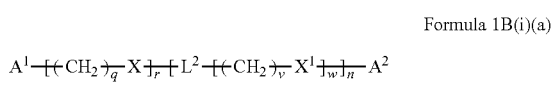

wherein
n is an integer from 1 to 5;
$A^1$ is an endcapping group;
$A^2$ is hydrogen or an endcapping group;
X and $X^1$ are each independently selected from OC(O)O, C(O)O and O;
q and v are each independently selected from an integer of 1 to 50 (for example 5 to 20); and
r and w are each independently selected from an integer of 2 to 50.

The block copolymer segment may be a block copolymer segment of Formula 1B(i)(b):

Formula 1B(i)(b)
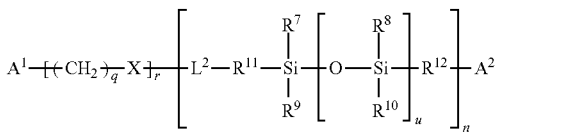

wherein each $A^1$, $A^2$, q, X, and r, are as defined in claim 1, and $L^2$, n, $R^7$, $R^8$, $R^9$, $R^{10}$, $R^{11}$, $R^{12}$ and u, are as defined herein.

The block copolymer segment may be a block copolymer segment of Formula 1B(ii):

Formula 1B(ii)
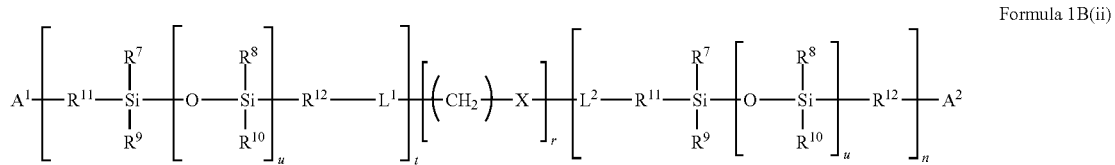

wherein each $A^1$, $A^2$, $L^1$, $L^2$, X, n, q, r and t, are as defined in claim 1, and each $R^7$, $R^8$, $R^9$, $R^{10}$, $R^{11}$, $R^{12}$ and u, are as defined herein.

Substituent Q

Substituent Q may be selected from a moiety of Formula A or Formula B as described herein.

Substituent Q may be selected from a moiety of Formula A:

Formula A
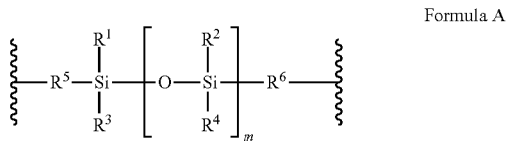

wherein
$R^1$, $R^2$, $R^3$, and $R^4$, are each independently selected from hydrogen and an optionally substituted straight chain, branched or cyclic, saturated and unsaturated hydrocarbon radical;
$R^5$ and $R^6$ are each independently selected from a straight chain, branched or cyclic, saturated and unsaturated hydrocarbon radical optionally interrupted with one or more heteroatoms independently selected from O, N and S;
m is an integer of 1 to 50.

Substituent Q may be selected from a moiety of Formula B:

Formula B
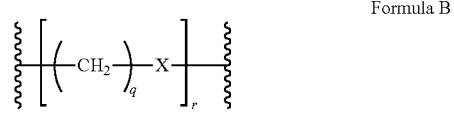

wherein
X is a group selected from OC(O)O, C(O)O and O;
q is an integer of 1 to 50; and
r is an integer of 2 to 50.

In one embodiment substituent Q is a moiety of Formula A. Q may be α,ω bis-(6-hydroxyethoxypropyl)polydimethylsiloxane. In another embodiment substituent Q is a moiety of Formula B.

Substituent $A^1$

Herein, substituent $A^1$ is an "endcapping group" and includes reactive functional groups or groups containing reactive functional groups. Examples of suitable reactive functional groups for substituent $A^1$ include: hydroxyl groups, carboxylic acids, aldehydes, ketones, esters, acid halides, acid anhydrides, amine groups, imine groups, thio groups, thioesters, sulphonic acids and epoxides.

$A^1$ may be selected from hydroxyl or amine. In one embodiment, $A^1$ is a hydroxyl group. In another embodiment, $A^1$ is an amine group.

Substituent $A^2$

Herein substituent $A^2$ is hydrogen or an "endcapping group" and includes reactive functional groups or groups containing reactive functional groups. Examples of suitable reactive functional groups for substituent $A^2$ include: hydroxyl groups, carboxylic acids, aldehydes, ketones, esters, acid halides, acid anhydrides, amine groups, imine groups, thio groups, thioesters, sulphonic acids and epoxides.

$A^2$ may be selected from hydrogen, hydroxyl or amine. In one embodiment $A^2$ is hydrogen. In one embodiment $A^2$ is an endcapping group. In another embodiment $A^2$ is a hydroxyl group. In another embodiment $A^2$ is an amine group.

Substituents $Y^1$ and $Y^2$

Herein each individual substituent $Y^1$ and $Y^2$ may be independently selected from a polysiloxane macrodiol, polysiloxane macrodiamine, polyether macrodiol, polycarbonate macrodiol, polyester macrodiol, or a polyhydrocarbon macrodiol.

At least one of $Y^1$ and $Y^2$ may be a polysiloxane macrodiol. $Y^1$ may be a polysiloxane macrodiol. $Y^2$ may be a polysiloxane macrodiol.

Examples of polysiloxane macrodiols include, but are not limited to: polydimethylsiloxane diols, such as α,ω bis-(6-hydroxyethoxypropyl)polydimethylsiloxane, α,ω bis-(4-hydroxybutyl)polydimethylsiloxane and α,ω bis-(3-hydroxypropyl)polydimethylsiloxane.

In one embodiment at least one of $Y^1$ and $Y^2$ is a polydimethylsiloxane diol. In another embodiment both of $Y^1$ and $Y^2$ are polydimethylsiloxane diols. In another embodiment at least one of $Y^1$ and $Y^2$ is α,ω bis-(6-hydroxyethoxypropyl)polydimethylsiloxane. In another embodiment both of $Y^1$ and $Y^2$ are α,ω bis-(6-hydroxyethoxypropyl)polydimethylsiloxane.

At least one of $Y^1$ and $Y^2$ may be a polysiloxane macrodiamine. $Y^1$ may be a polysiloxane macrodiamine. $Y^2$ may be a polysiloxane macrodiamine.

Examples of polysiloxane macrodiamines include, but are not limited to: α,ω bis-(aminomethyl)polydimethylsiloxane, α,ω bis-(2-aminoethyl)polydimethylsiloxane, α,ω bis-(3-aminopropyl)polydimethylsiloxane, α,ω bis-(4-aminobutyl)polydimethylsiloxane, α,ω bis-(5-aminopentyl)polydimethylsiloxane and the like.

At least one of $Y^1$ and $Y^2$ may be a polyether macrodiol. $Y^1$ may be a polyether macrodiol. $Y^2$ may be a polyether macrodiol.

Examples of polyether macrodiols include, but are not limited to: poly(ethylene oxide), poly(propylene oxide), poly(butylene oxide), poly(pentylene oxide), poly(hexamethylene oxide) (PHMO), poly(heptamethylene oxide), poly(octamethylene oxide) (POMO) and poly(decamethylene oxide) (PDMO).

In one embodiment at least one of $Y^1$ and $Y^2$ is poly(hexamethylene oxide) (PHMO).

In one embodiment both of $Y^1$ and $Y^2$ are poly(hexamethylene oxide) (PHMO).

At least one of $Y^1$ and $Y^2$ may be a polycarbonate macrodiol. $Y^1$ may be a polycarbonate macrodiol. $Y^2$ may be a polycarbonate macrodiol.

Examples of polycarbonate macrodiols include, but are not limited to: poly(propylene carbonate), poly(hexamethylene carbonate) and polycarbonate and copolycarbonate macrodiols can be prepared by using an ester interchange reaction as described in P. A. Gunatillake et al., *Journal of Applied Polymer Science*, 69(8) 1621-1633, 1998, for example by reacting a carbonate such as ethylene carbonate with a diol. Appropriate diols include, but are not limited to: 1,6-hexanediol, 1,10-decanediol, 2,2-diethyl-1,3-propanediol, 1,4-cyclohexanedimethanol and his(4-hydroxybutyl)-1,1,3,3-tetramethyldisiloxane.

At least one of $Y^1$ and $Y^2$ may be a polyester macrodiol. $Y^1$ may be a polyester macrodiol. $Y^2$ may be a polyester macrodiol.

Examples of polyester macrodiols include, but are not limited to: poly(caprolactone)diol, poly(tetramethyleneadipate)diol, poly(D,L-lactide) and, poly(glycolide).

At least one of $Y^1$ and $Y^2$ may be a polyhydrocarbon macrodiol. $Y^1$ may be a polyhydrocarbon macrodiol. $Y^2$ may be a polyhydrocarbon macrodiol.

Examples of polyhydrocarbon macrodiols include polymeric aliphatic α,ω-diols. Specific examples of polyhydrocarbon macrodiols include, but are not limited to: poly(isobutylene)diol and poly(butadiene)diols, such as hydrogenated poly(butadiene)diols (including fully hydrogenated poly(butadiene)diols).

In one embodiment, $Y^1$ and $Y^2$ are each independently selected from a moiety of Formula A' or Formula B':

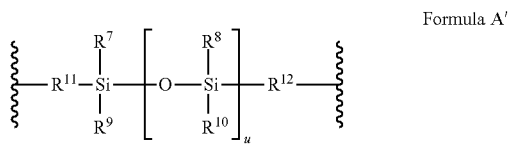

Formula A' wherein
$R^7$, $R^8$, $R^9$, and $R^{10}$, are each independently selected from hydrogen and an optionally substituted straight chain, branched or cyclic, saturated and unsaturated hydrocarbon radical; and $R^{11}$ and $R^2$ are each independently selected from a straight chain, branched or cyclic, saturated and unsaturated hydrocarbon radical optionally interrupted with one or more heteroatoms independently selected from O, N and S; and u is an integer of 1 to 50, or

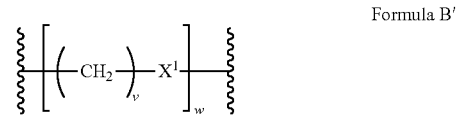

Formula B' wherein
X¹ is a group selected from OC(O)O, C(O)O and O;
v is an integer of 1 to 50, for example an integer of 5 to 20; and
w is an integer of 2 to 50.

In one embodiment at least one of Y¹ and Y² is a moiety of Formula A'.

In one embodiment at least one of Y¹ and Y² is a moiety of Formula B'.

In another embodiment substituents Y¹ and Y² are the same.

In yet another embodiment substituents Y¹ and Y² are different. It will be appreciated that Y¹ and Y² may be selected from different groups within same individual Formula A'. Similarly, it will also be appreciated that Y¹ and Y² may be selected from different groups within same individual Formula B'.

Substituents L¹ and L²

Herein substituents L¹ and L² are divalent linking groups independently selected from urethane, urea, urea carbonate, amide, ester, and phosphonate linking groups.

At least one of L¹ or L² may be a urethane linking group. L¹ may be a urethane linking group. L² may be a urethane linking group.

Urethane linking groups can be produced by reacting hydroxyl containing compounds, such as a macrodiol, with a diisocyanate. Examples of appropriate diisocyanates include aliphatic, cyclic or aromatic diisocyanates such as, for example: 1,4-diisocyanatobutane, 1,12-diisocyanatododecane, 1,6-diisocyantehexane, 1,8-diisocyanateoctane, 4,4'-methylenediphenyl diisocyanate (methylenebis(cyclohexyl diisocyanate) (H12MDI), p-phenylene diisocyanate (p-PDI), m-phenylene diisocyanate (m-PDI) trans-cyclohexane-1,4-diisocyanate (CHDI) or a mixture of the cis and trans isomers, 1,6-hexamethylene diisocyanate (HDI), 2,4-toluene diisocyanate (2,4-TDI) or its isomers (for example 2,6-toluene diisocyanate (2,6-TDI)), or mixtures thereof, p-tetramethylxylene diisocyanate (p-TMXDI), isophorone diisocyanate or m-tetramethylxylene diisocyanate (m-TMXDI), 1,6-diisocyanatohexane (DICH), 1,3-bis(1-isocyanato-1-methylethyl)benzene, or 1,5-diisocyanatonaphthalene (NDI).

In one embodiment, L¹ or L² may be independently a linking group of Formula E:

Formula E

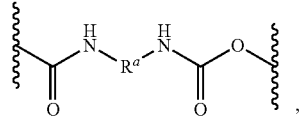

wherein R^a is selected from:
  an optionally substituted straight chain, branched or cyclic, saturated or unsaturated hydrocarbon radical (including optionally substituted alkyl, alkenyl, alkynyl, aryl or heterocyclyl radicals).
For example, L¹ or L² may be selected from:

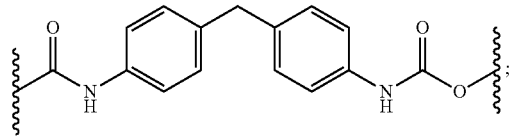

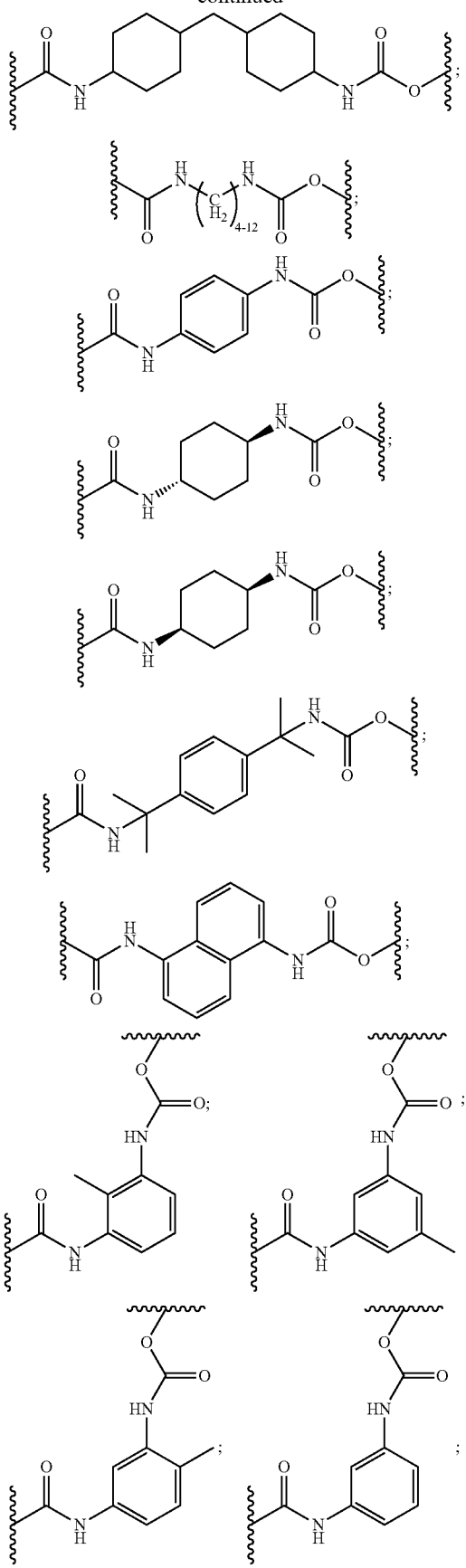

-continued

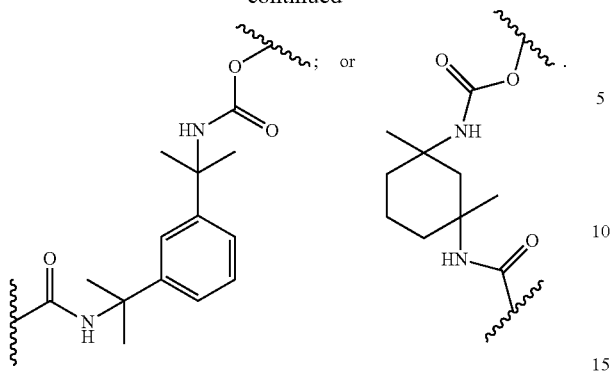 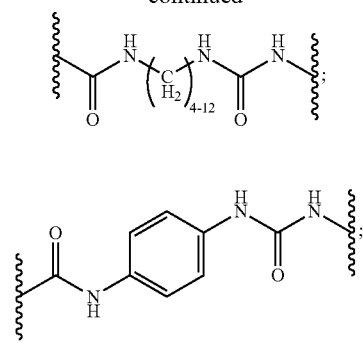

At least one of $L^1$ or $L^2$ may be a urea linking group. $L^1$ may be a urea linking group. $L^2$ may be a urea linking group.

Urea linking groups can be produced by reacting amine containing compounds, such as a macrodiamine, with a diisocyanate. Examples of appropriate diisocyanates include aliphatic, cyclic or aromatic diisocyanates such as, for example: 1,4-diisocyanatobutane, 1,12-diisocyanatododecane, 1,6-diisocyantehexane, 1,8-diisocyanateoctane, 4,4'-methylenediphenyl diisocyanate (MDI), 4,4'-methylenebis (cyclohexyl diisocyanate) (H12MDI), p-phenylene diisocyanate (p-PDI), m-phenylene diisocyanate (m-PDI) trans-cyclohexane-1,4-diisocyanate (CHDI) or a mixture of the cis and trans isomers, 1,6-hexamethylene diisocyanate (HDI), 2,4-toluene diisocyanate (2,4-TDI) or its isomers (for example 2,6-toluene diisocyanate (2,6-TDI)), or mixtures thereof, p-tetramethylxylene diisocyanate (p-TMXD1), isophorone diisocyanate or m-tetramethylxylene diisocyanate (m-TMXDI), or 1,5-diisocyanatonaphthalene (NDI).

In one embodiment, $L^1$ or $L^2$ may be independently a linking group of Formula F:

Formula F

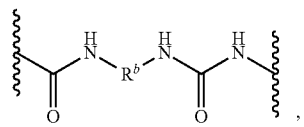

wherein $R^b$ is selected from:
  an optionally substituted straight chain, branched or cyclic, saturated or unsaturated hydrocarbon radical (including optionally substituted alkyl, alkenyl, alkynyl, aryl or heterocyclyl radicals).

For example, $L^1$ or $L^2$ may be selected from:

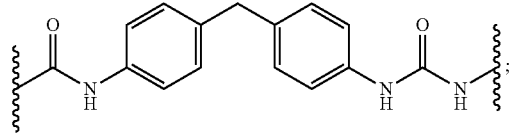

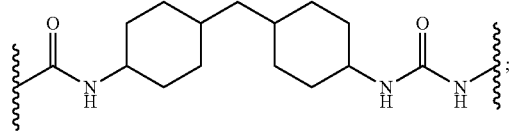

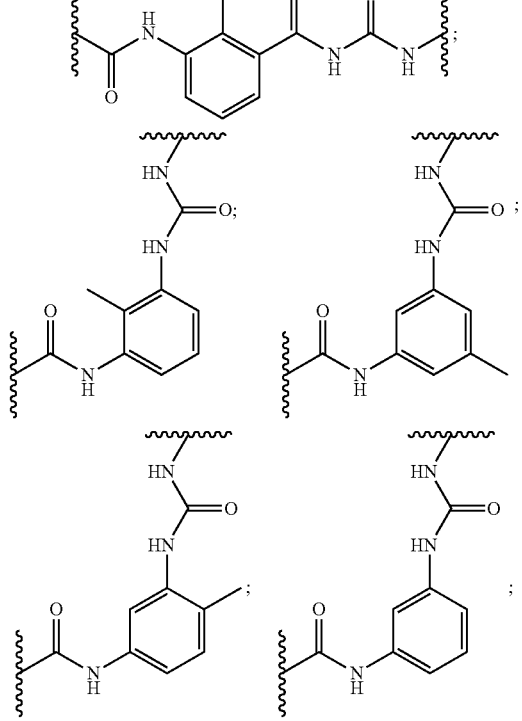

-continued

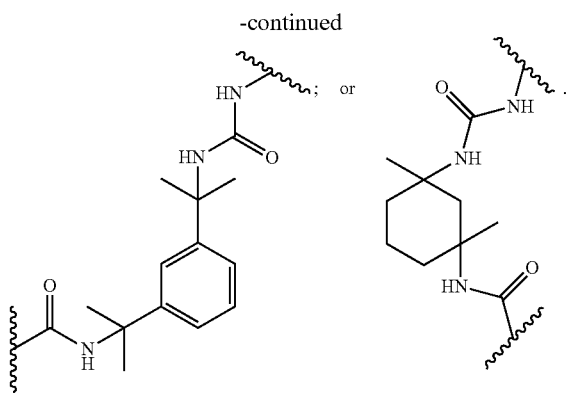

At least one of $L^1$ or $L^2$ may be a carbonate linking group. $L^1$ may be a carbonate linking group. $L^2$ may be a carbonate linking group.

In one embodiment, $L^1$ or $L^2$ may be independently a linking group of Formula G:

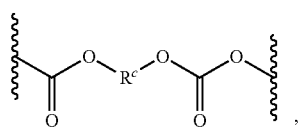

Formula G wherein $R^c$ is selected from an optionally substituted straight chain, branched or cyclic, saturated or unsaturated hydrocarbon radical (including optionally substituted alkyl, alkenyl, alkynyl, aryl or heterocyclyl radicals).

At least one of $L^1$ or $L^2$ may be an amide linking group. $L^1$ may be an amide linking group. $L^2$ may be an amide linking group.

Examples of amide linking groups include —C(O)NH— groups.

At least one of $L^1$ or $L^2$ may be an ester linking group. $L^1$ may be an ester linking group. $L^2$ may be an ester linking group.

Examples of ester linking groups include, but are not limited to, esters formed through the reactions between alcohols and aliphatic or aromatic di-acid or diacid chloride containing compounds.

At least one of $L^1$ or $L^2$ may be a phosphonate linking group. $L^1$ may be a phosphonate linking group. $L^2$ may be a phosphonate linking group.

$L^1$ or $L^2$ ma be independently a linking group of Formula H:

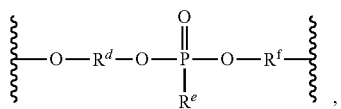

Formula H wherein:
each of $R^d$, and $R^f$ is each independently selected from: an optionally substituted straight chain, branched or cyclic, saturated or unsaturated hydrocarbon radical (including optionally substituted alkyl, alkenyl, alkynyl, aryl or heterocyclyl radicals); and
$R^e$ is selected from: hydrogen; or an optionally substituted straight chain, branched or cyclic, saturated or unsaturated hydrocarbon radical (including optionally substituted alkyl, alkenyl, alkynyl, aryl or heterocyclyl radicals). For example, substituent $R^c$ may be an optionally substituted methyl group.

In one embodiment substituents $L^1$ and $L^2$ are the same. In another embodiment substituents $L^1$ and $L^2$ are different. Substituents $R^1$, $R^2$, $R^3$, $R^4$, $R^5$, $R^6$, $R^7$, $R^8$, $R^9$, $R^{10}$, $R^{11}$ and $R^{12}$ Herein, $R^1$, $R^2$, $R^3$, $R^4$, $R^7$, $R^8$, $R^9$, and $R^{10}$ are each independently selected from hydrogen and an optionally substituted straight chain, branched or cyclic, saturated and unsaturated hydrocarbon radical (including optionally substituted alkyl, alkenyl, alkynyl, aryl or heterocyclyl radicals).

Herein. $R^5$, $R^6$, $R^{11}$ and $R^{12}$ are each independently selected from an optionally substituted straight chain, branched or cyclic, saturated and unsaturated hydrocarbon radical optionally interrupted with one or more heteroatoms independently selected from O, N and S (including optionally substituted alkyl, alkenyl, alkynyl, aryl or heterocyclyl radicals).

In one embodiment at least one of $R^1$, $R^2$, $R^3$, and $R^4$ is an optionally substituted alkyl group, including optionally substituted methyl, ethyl, propyl or butyl groups. For example at least one of $R^1$, $R^2$, $R^3$, and $R^4$ is a methyl group.

In one embodiment each of $R^1$, $R^2$, $R^3$, and $R^4$ is an optionally substituted alkyl group, including optionally substituted methyl, ethyl, propyl or butyl groups. For example each of $R^1$, $R^2$, $R^3$, and $R^4$ is a methyl group.

In one embodiment at least two of $R^1$, $R^2$, $R^3$, and $R^4$ are the same substituent.

In one embodiment all of $R^1$, $R^2$, $R^3$, and $R^4$ are the same substituent.

In another embodiment at least one of $R^5$ and $R^6$ is an optionally substituted alkyl or alkoxyalkyl group. For example at least one of $R^5$ and $R^6$ may be independently selected from optionally substituted: propylene, butylene, pentylene, hexylene, ethoxypropyl, propoxypropyl and butoxypropyl groups.

In another embodiment both of $R^5$ and $R^6$ are optionally substituted alkyl or alkoxyalkyl groups. For example both of $R^5$ and $R^6$ may be selected from optionally substituted: propylene, butylene, pentylene, hexylene, ethoxypropyl, propoxypropyl and butoxypropyl groups. For example both $R^5$ and $R^6$ may be ethoxypropyl.

In another embodiment at least one of $R^5$ and $R^6$ is independently selected from the moiety of Formula D':

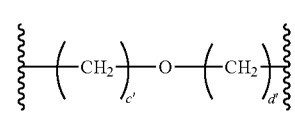

Formula D' wherein c' is an integer between 1 and 6; and d' is an integer between 1 and 6. For example c' is 2 and/or d' is 3.

In one embodiment $R^5$ and $R^6$ are the same substituent.
In one embodiment $R^5$ and $R^6$ are different substituents.
In one embodiment at least one of $R^7$, $R^8$, $R^9$, and $R^{10}$ is an optionally substituted alkyl group, including optionally substituted methyl, ethyl, propyl or butyl groups. For example at least one of $R^7$, $R^8$, $R^9$, and $R^{10}$ is a methyl group.

In one embodiment each of $R^7$, $R^8$, $R^9$, and $R^{10}$ is an optionally substituted alkyl group, including optionally substituted methyl, ethyl, propyl or butyl groups. For example each of $R^7$, $R^8$, $R^9$, and $R^{10}$ is a methyl group.

In one embodiment at least two of $R^7$, $R^8$, $R^9$, and $R^{10}$ are the same substituent.

In one embodiment all of $R^7$, $R^8$, $R^9$, and $R^{10}$ are the same substituent.

In another embodiment at least one of $R^{11}$ and $R^{12}$ is an optionally substituted alkyl or alkoxyalkyl group. For example at least one of $R^{11}$ and $R^{12}$ may be independently selected from optionally substituted: propylene, butylene, pentylene, hexylene, ethoxypropyl, propoxypropyl and butoxypropyl groups.

In another embodiment both of $R^{11}$ and $R^{12}$ are optionally substituted alkyl or alkoxyalkyl groups. For example both of $R^{11}$ and $R^{12}$ may be selected from optionally substituted: propylene, butylene, pentylene, hexylene, ethoxypropyl, propoxypropyl and butoxypropyl groups. For example both $R^{11}$ and $R^{12}$ may be ethoxypropyl.

In one embodiment, at least one of $R^{11}$ and $R^{12}$ is independently selected from the moiety of Formula C':

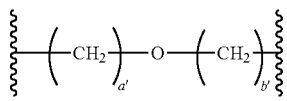

Formula C' wherein a' is an integer between 1 and 6; and b' is an integer between 1 and 6. For example a' is 2 and/or b' is 3.

In one embodiment $R^{11}$ and $R^{12}$ are the same substituent. In another embodiment $R^{11}$ and $R^{12}$ are different substituents.

Substituents X and $X^1$

Herein, substituent X and $X^1$ may be independently selected from OC(O)O, C(O)O and O.

X may be OC(O)O. X may be C(O)O. X may be O. $X^1$ may be OC(O)O. $X^1$ may be C(O)O. $X^1$ may be O. X and $X^1$ may be the same. X and $X^1$ may be different.

Integers a', b', c', d', m, m', m'', n, q, q', q'', r, r', r'', t, u, v and w

Integer a' may be: 1 or 2 or 3 or 4 or 5 or 6. In one embodiment, integer a' is 2. In another embodiment, integer a' is 3.

Integer b' may be: 1 or 2 or 3 or 4 or 5 or 6. In one embodiment, integer b' is 2. In another embodiment integer b' is 3.

Integer c' may be: 1 or 2 or 3 or 4 or 5 or 6. In one embodiment, integer c' is 2. In another embodiment, integer c' is 3.

Integer d' may be: 1 or 2 or 3 or 4 or 5 or 6. In one embodiment, integer d' is 2. In another embodiment integer d' is 3.

Herein integer m may be: 1 or 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 or 41 or 42 or 43 or 44 or 45 or 46 or 47 or 48 or 49 or 50.

Herein integer m' may be: 1 or 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 or 41 or 42 or 43 or 44 or 45 or 46 or 47 or 48 or 49 or 50.

Herein integer m'' may be: 1 or 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 or 41 or 42 or 43 or 44 or 45 or 46 or 47 or 48 or 49 or 50.

Herein integer n may be: 1 or 2 or 3 or 4 or 5.

Herein integer t may be: 0 or 1 or 2 or 3 or 4 or 5.

In one embodiment integer t is 0.

Herein integer q may be: 1 or 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 or 41 or 42 or 43 or 44 or 45 or 46 or 47 or 48 or 49 or 50.

In one embodiment integer q may be 5 or 6 or 7 or 8 or 9 or 10 or 11 or 12 or 13 or 14 or 15 or 16 or 17 or 18 or 19 or 20.

Herein, q may be in a range of 1 to 10, for example in a range of 2 to 6.

Herein integer q' may be: 1 or 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 or 41 or 42 or 43 or 44 or 45 or 46 or 47 or 48 or 49 or 50.

In one embodiment integer q' may be 5 or 6 or 7 or 8 or 9 or 10 or 11 or 12 or 13 or 14 or 15 or 16 or 17 or 18 or 19 or 20.

Herein, q' may be in a range of 1 to 10, for example in a range of 2 to 6.

Herein integer q'' may be: 1 or 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 or 41 or 42 or 43 or 44 or 45 or 46 or 47 or 48 or 49 or 50.

In one embodiment integer q'' may be 5 or 6 or 7 or 8 or 9 or 10 or 11 or 12 or 13 or 14 or 15 or 16 or 17 or 18 or 19 or 20.

Herein, q'' may be in a range of 1 to 10, for example in a range of 2 to 6.

Herein integer r may be: 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 or 41 or 42 or 43 or 44 or 45 or 46 or 47 or 48 or 49 or 50.

Herein integer r' may be: 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 or 41 or 42 or 43 or 44 or 45 or 46 or 47 or 48 or 49 or 50.

Herein integer r'' may be: 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 or 41 or 42 or 43 or 44 or 45 or 46 or 47 or 48 or 49 or 50.

Herein integer u may be: 1 or 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 or 41 or 42 or 43 or 44 or 45 or 46 or 47 or 48 or 49 or 50.

Herein integer v may be: 1 or 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 or 41 or 42 or 43 or 44 or 45 or 46 or 47 or 48 or 49 or 50.

In one embodiment integer v may be 5 or 6 or 7 or 8 or 9 or 10 or 11 or 12 or 13 or 14 or 15 or 16 or 17 or 18 or 19 or 20.

Herein, v may be in a range of 1 to 10.

Herein integer w may be: 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 or 41 or 42 or 43 or 44 or 45 or 46 or 47 or 48 or 49 or 50.

In one embodiment integer w may be 5 or 6 or 7 or 8 or 9 or 10 or 11 or 12 or 13 or 14 or 15 or 16 or 17 or 18 or 19 or 20.

Herein, w may be in a range of 2 to 10.

It will be appreciated that the above integer embodiments includes any integer range thereof. For example, a range may be provided between any two integers selected from each of the above described integer embodiments of a', b', c', d', m, m', m'', n, q, q', q'', r, r', r'', t, u, v and w.

The block copolymer segment of Formula 1 according to any of the above described embodiments may have a molecular weight range between about 400 and 6000, or about 400 and 4000, or about 800 and 1600. Unless stated otherwise, herein the phrase "molecular weight" refers to the number-average molecular weight ($M_n$) of a particular polymer.

Thermoplastic Polyurethane or Polyurethaneurea Elastomer Materials

Disclosed herein is a thermoplastic polyurethane or polyurethaneurea elastomer material comprising a plurality of soft segments and hard segments, wherein the plurality of soft segments are each derived from at least one block copolymer segment of Formula 1 as defined herein and optionally an additional polyol or polyamine.

A thermoplastic polyurethane or polyurethaneurea elastomer material may be provided comprising a plurality of soft segments and hard segments, wherein the plurality of soft segments are each derived from a single type of block copolymer segment selected from a block copolymer segment of Formula 1 as defined herein and optionally an additional polyol or polyamine.

Also disclosed herein is a thermoplastic polyurethane or polyurethaneurea elastomer material comprising a plurality of soft segments and hard segments, wherein the plurality of soft segments are each derived from a mixture of two separate block copolymer segments of Formula 1 as defined herein and optionally an additional polyol or polyamine.

Also disclosed herein are thermoplastic polyurethane or polyurethaneurea elastomer materials comprising a reaction product of:
i. at least one block copolymer segment of Formula 1 as defined herein;
ii. a diisocyanate;
iii. one or more chain extenders; and
iv. optionally an additional polyol or polyamine.

Herein, the thermoplastic polyurethane or polyurethaneurea elastomer material may have a tensile strength of 25 MPa. For example the thermoplastic polyurethane or polyurethaneurea elastomer material may have a tensile strength of: ≥7.5 MPa, or ≥10 MPa, or ≥12.5 MPa, or ≥15 MPa, or ≥17.5 MPa, or ≥20 MPa, or ≥22.5 MPa, or ≥25 MPa, or ≥27.5 MPa, or ≥30 MPa, or ≥32.5 MPa, or ≥35 MPa, or ≥37.5 MPa, or ≥40 MPa, or ≥42.5 MPa, or ≥45 MPa, or ≥47.5 MPa, or ≥50 MPa.

Herein, the thermoplastic polyurethane or polyurethaneurea elastomer material may have a Young's Modulus of ≥10 MPa. For example the thermoplastic polyurethane or polyurethaneurea elastomer material may have a Young's Modulus of: ≥12.5 MPa, or ≥15 MPa, or ≥17.5 MPa, or ≥20 MPa, or ≥22.5 MPa, or ≥25 MPa, or ≥27.5 MPa, or ≥30 MPa, or ≥32.5 MPa, or ≥35 MPa, or ≥37.5 MPa, or ≥40 MPa, or ≥42.5 MPa, or ≥45 MPa, or ≥47.5 MPa, or ≥50 MPa, or ≥52.5 MPa, or ≥55 MPa, or ≥57.5 MPa, or ≥60 MPa, or ≥62.5 MPa, or ≥65 MPa, or ≥67.5 MPa, or ≥70 MPa, or ≥72.5 MPa, or ≥75 MPa, or ≥77.5 MPa, or ≥80 MPa.

Herein, the thermoplastic polyurethane or polyurethaneurea elastomer material may have an elongation at break of ≥500%. For example the thermoplastic polyurethane or polyurethaneurea elastomer material may have an elongation at break of: ≥550%, or ≥600%, or ≥650%, or ≥700%, or ≥750%, or ≥800%, or ≥850%, or ≥900%, or ≥950% or ≥1000%, or ≥1050%, or ≥1100% or ≥1150%, or ≥1200%, or ≥1250%, or ≥1300%, or ≥1350%, or ≥1400%, or ≥1450%, or ≥1500%, or ≥1550%, or ≥1600%, or ≥1650%, or ≥1700%, or ≥1750%, or ≥1800%, or ≥1850%, or ≥1900%, or ≥1950%, or ≥2000%.

It will be appreciated that these tensile strengths may be measured using standard industry methods, for example a method adopted from ASTM Standard Method for thin Plastic Sheeting (e.g. ASTM D 882-02). In a further example, the method may involve thin films, for example about 200 to 300 microns, using the ASTM D 882-02 test method.

Example conditions which may be used to measure the tensile strength of a sample with ASTM D 882-02 method are:
using dumbbell shaped specimens which are 75 mm in length, 13 mm in width at each end and 4 mm at the central narrow section (with a constant width over at least 15 mm of length); and
using an Instron 5565 fitted with static load cell ±100 N and calibrated using Instron Bluehill 2 (version 2.35) software.

For the tensile test with dry conditions, the specimen may be:
fixed between upper and lower grips (for example Instron grips) such that the gap between the grips is 10 mm;
stretching the 10 mm long section of film at a rate of 50 mm per minute until the film breaks;
performing at least three replicates, for example three, four or five replicates.

For the tensile test with wet conditions, or replicating the conditions found for medical applications, the specimen may be:
placed in a plastic bag and immersed in water maintained at 37° C. for at least two hours;
dried using tissue paper and fixed between upper and lower grips (for example Instron grips) such that the gap between the grips is 10 mm;
stretched at a rate of 100 mm per min until the film breaks.

Stress, strain, breaking stress and elongation at breaking can be obtained using either the dry or wet conditions from the Instron Bluchill 2 (version 2.35) software. These parameters allow one to obtain values for the tensile strength, the Young's modulus (stiffness) and Elongation (elasticity) for a sample.

Herein, the thermoplastic polyurethane or polyurethaneurea elastomer material may have a polydispersity index (PDI) of ≤3.00. For example the thermoplastic polyurethane or polyurethaneurea elastomer material may have a PDI of ≤2.50, ≤2.00, or ≤1.50.

In one embodiment a single block copolymer segment of Formula 1 is used in the formulation of the thermoplastic polyurethane or polyurethaneurea elastomer material.

In another embodiment two different block copolymer segments of Formula 1 are used in the formulation of the thermoplastic polyurethane or polyurethaneurea elastomer material.

Examples of mixtures one or two different block copolymer segments of Formula 1 or a combination of a block copolymer of Formula 1 and a macrodiol, which are used in the formulation of a thermoplastic polyurethane or polyurethaneurea elastomer material, are shown in Table 1. Here Segment 1 and/or Segment 2 can be added in a reaction mixture with one or more chain extenders, a diisocyanate, to produce a thermoplastic polyurethane or polyurethaneurea elastomer material. In these examples $R^{5a}$ and $R^{6a}$ may both be —$(CH_2)_2O(CH_2)_4$—.

Table 1—Examples of one or two different block copolymer segments of Formula 1, or a combination of a block copolymer of Formula 1 and a macrodiol, which are used in the formulation of a thermoplastic polyurethane or polyurethaneurea elastomer material. In the following examples, $R^{5a}$, $R^{6a}$, m' and r are as defined herein.

| Group | Segment Number for Block Copolymer | Specific Segment for Block Copolymer |
|---|---|---|
| 1 | Segment 1 | 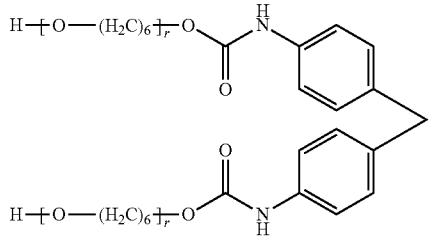 |
|   | Segment 2 | — |
| 2 | Segment 1 | 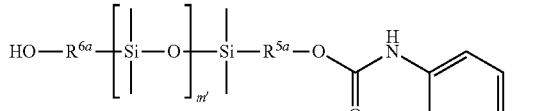 |
|   | Segment 2 | — |
| 3 | Segment 1 | 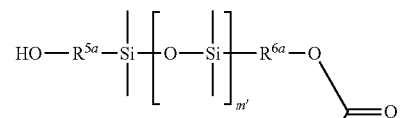 |
|   | Segment 2 | — |
| 4 | Segment 1 | 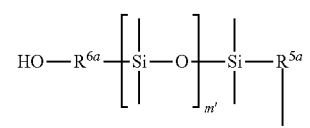 |
|   | Segment 2 | — |

-continued
| Group | Segment Number for Block Copolymer | Specific Segment for Block Copolymer |
|---|---|---|
| 5 | Segment 1 | 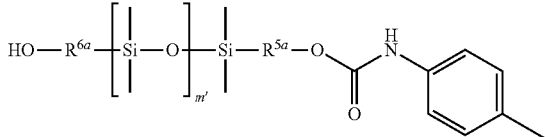 |
|   | Segment 2 | HO—[(CH$_2$)$_6$—O]$_r$—H |
| 6 | Segment 1 | 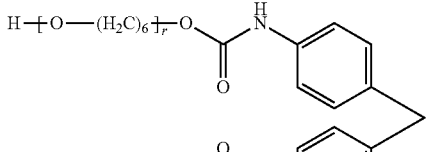 |
|   | Segment 2 | 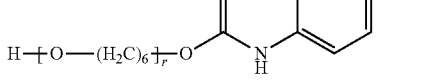 |
| 7 | Segment 1 | 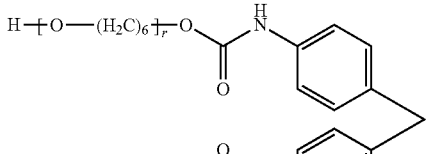 |
|   | Segment 2 | 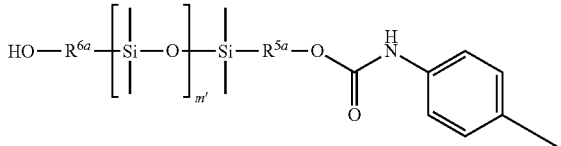 |

| Group | Segment Number for Block Copolymer | Specific Segment for Block Copolymer |
|---|---|---|
| 8 | Segment 1 | $HO-R^{5a}-Si\left[-O-Si\right]_{m'}-R^{6a}-O$ <br> $HO-R^{6a}\left[-Si-O\right]_{m'}-Si-R^{5a}-O$ <br> connected to $C=O$ |
|  | Segment 2 | $HO-[(CH_2)_6-O]_r-H$ |

Diisocyanates

Examples of appropriate diisocyanates include but are not limited to: aliphatic, cyclic or aromatic diisocyanates such as, for example: 1,4-diisocyanatobutane, 1,12-diisocyanatododecane, 1,6-diisocyantehexane, 1,8-diisocyanateoctane, 4,4'-methylenediphenyl diisocyanate (MDI), 4,4'-methylenbis(cyclohexyl diisocyanate) (H12MDI), p-phenylene diisocyanate (p-PDI), m-phenylene diisocyanate (m-PDI) trans-cyclohexane-1,4-diisocyanate (CHDI) or a mixture of the cis and trans isomers, 1,6-hexamethylene diisocyanate (HDI), 2,4-toluene diisocyanate (2,4-TDI) or its isomers (for example 2,6-toluene diisocyanate (2,6-TDI)), or mixtures thereof, p-tetramethylxylene diisocyanate (p-TMXDI), isophorone diisocyanate or m-tetramethylxylene diisocyanate (m-TMXDI), or 1,5-diisocyanatonaphthalene (NDI).

In one embodiment, the diisocyanate is MDI.

Chain Extender

Herein at least one chain extender is included in the formation of the thermoplastic polyurethane or polyurethaneurea elastomer materials. A chain extender is a compound that has two functional groups per molecule, such as diols or diamines, which are capable of reacting with an isocyanate group.

The chain extender may have a molecular weight range of 400 or less. Alternatively, the chain extender may have a molecular weight range of about 800 to about 1600. In another embodiment the chain extender may have a molecular weight range of about 400 to about 4000.

The chain extender may be selected from diol or diamine chain extenders. In one embodiment at least one chain extender is a diol.

Examples of diol chain extenders include, but are not limited to: $C_{1-12}$ alkane diols such as: 1,4-butanediol, 1,6-hexanediol, 1,8-octanediol, 1,9-nonanediol and 1,10-decanediol, 1,4-cyclohexane dimethanol, p-xyleneglycol, 1,4-bis (2-hydroxyethoxy) benzene, 1,12-dodecanediol and 1,3bis-(4-hydroxybutyl)1,1,3,3-tetramethyldisiloxane.

In one embodiment at least one chain extender is a diamine. Suitable diamine chain extenders include $C_{1-12}$ alkane diamines such as 1,2-ethylenediamine, 1,3-propanediamine, 1,4-butanediamine, 1,3bis-(3-aminopropyl) tetramethyldisiloxane, or 1,3bis-(3-aminobutyl) tetramethyldisiloxane.

The wt % of a hard segment in a thermoplastic polyurethane or polyurethaneurea (the wt % determined by the weight of a linking compound (for example a diisocyanate)+ chain extender as a percentage of the total weight of the polyurethane/polyurethaneurea) may be in a range of about 20 wt % to about 60 wt %. Exemplified ranges include: about 30 wt % to about 60 wt %, or about 40 wt % to about 60 wt %, about 50 wt % to about 60 wt % and about 40 wt % to about 50 wt %.

In one embodiment only one chain extender is used in the formation of the thermoplastic polyurethane or polyurethaneurea elastomer material.

In one embodiment two chain extenders are used in the formation of the thermoplastic polyurethane or polyurethaneurea elastomer material. For example a combination of 1,4-butanediol and ethylene diamine.

Additional Polyol or Polyamine

Herein a thermoplastic polyurethane or polyurethaneurea elastomer materials comprising a reaction product of: at least one block copolymer segment of Formula 1 as defined herein; a diisocyanate; and one or more chain extenders, may include an additional polyol or polyamine.

The additional polyols may include poly(hexamethylene oxide), poly(heptamethylene oxide), poly(octamethylene oxide) (POMO), poly(decamethylene oxide) (PDMO), polydimethylsiloxane diols, poly(butadine diol), poly(carbonate) diol poly(isobutylene)diol, or a mixture thereof.

In one embodiment the additional polyol may be: a polydimethylsiloxane polymer comprising at least two hydroxyl groups, for example α,ω bis-(6-hydroxyethoxypropyl)polydimethylsiloxane.

In one embodiment the additional polyol is a polyol of Formula J:

Formula J

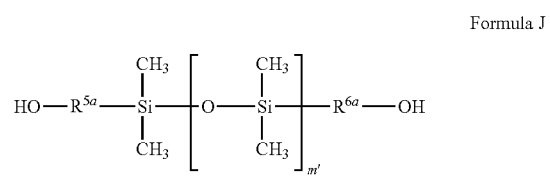

wherein:
R$^{5a}$ and R$^{6a}$ are each independently selected from a straight chain, branched or cyclic, saturated and unsaturated hydrocarbon radical optionally interrupted with one or more heteroatoms independently selected from O, N and S; and m' is an integer of 1 to 50.

$R^{5a}$ and $R^{6a}$ may be independently selected from optionally substituted alkyl or alkoxyalkyl groups. For example $R^{5a}$ and $R^{6a}$ may be independently selected from optionally substituted: propylene, butylene, pentylene, hexylene, ethoxypropyl, propoxypropyl and butoxypropyl groups.

In another embodiment both of $R^{5a}$ and $R^{6a}$ are optionally substituted alkyl or alkoxyalkyl groups. For example $R^{5a}$ and $R^{6a}$ may both be selected from optionally substituted: propylene, butylene, pentylene, hexylene, ethoxypropyl, propoxypropyl and butoxypropyl groups. For example both $R^{5a}$ and $R^{6a}$ may be ethoxypropyl.

$R^{5a}$ and $R^{6a}$ may both be $(CH_2)_2O(CH_2)_3$.

In another embodiment the additional polyol is a polyol of Formula K':

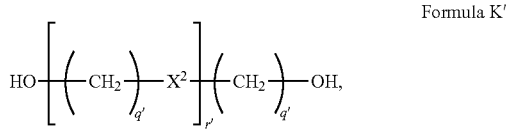

Formula K' wherein:
$X^2$ is a group selected from: OC(O)O, C(O)O and O;
q' is an integer of 1 to 50, including, for example, an integer of 5 to 20; and
r' is an integer of 1 to 50.

In one embodiment $X^2$ is O.

In another embodiment the additional polyol is selected from: poly(hexamethylene oxide), poly(heptamethylene oxide), poly(octamethylene oxide) (POMO) and poly(decamethylene oxide) (PDMO).

The additional polyamines may include α,ω bis-(3-aminopropyl)polydimethylsiloxane, α,ω bis-(aminomethyl)polydimethylsiloxane, α,ω bis-(2-aminoethyl)polydimethylsiloxane, α,ω bis-(4-aminobutyl)polydimethylsiloxane, α,ω bis-(5-aminopentyl)polydimethylsiloxane and the like.

The additional polyamine may be a polyamine of Formula L:

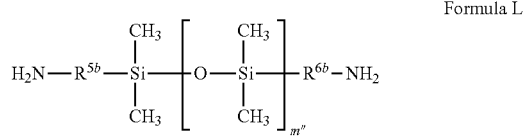

Formula L wherein:
$R^{5b}$ and $R^{6b}$ are each independently selected from a straight chain, branched or cyclic, saturated and unsaturated hydrocarbon radical optionally interrupted with one or more heteroatoms independently selected from O, N and S; and
m" is an integer of 1 to 50.

$R^{5b}$ and $R^{6b}$ may be independently selected from optionally substituted alkyl or alkoxyalkyl groups. For example $R^{5b}$ and $R^{6b}$ may be independently selected from optionally substituted: propylene, butylene, pentylene, hexylene, ethoxypropyl, propoxypropyl and butoxypropyl groups.

In another embodiment both of $R^{5b}$ and $R^{6b}$ are optionally substituted alkyl or alkoxyalkyl groups. For example $R^{5b}$ and $R^{6b}$ may both be selected from optionally substituted: propylene, butylene, pentylene, hexylene, ethoxypropyl, propoxypropyl and butoxypropyl groups. For example both $R^{5a}$ and $R^{6a}$ may be ethoxypropyl.

$R^{5b}$ and $R^{6b}$ may both be $(CH_2)_2O(CH_2)_3$.

The additional polyamine may be a polyamine of Formula M':

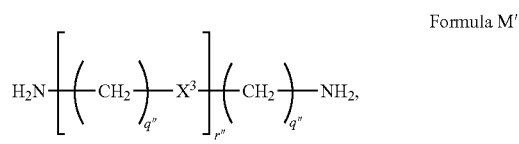

Formula M' wherein:
$X^3$ is a group selected from: OC(O)O, C(O)O and O;
q" is an integer of 1 to 50, including, for example, an integer of 5 to 20; and
r" is an integer of 1 to 50.

Processes for Preparing "Soft" Block Copolymers and Polyurethane or Polyurethaneurea Elastomer Materials Disclosed herein is a process for preparing a block copolymer segment of Formula 1, whereby the process comprising the step of combining:
  i. at least one macrodiol; or
  ii. at least one macrodiamine; or
  iii. a mixture of at least one macrodiol and at least one macrodiamine, with a divalent linking compound.

Optional additional steps may include one or more of:
  i. filtration;
  ii. the removal of solvent(s), for example via evaporation under reduced pressure; and/or
  iii. purification, for example by distillation (such as distillation via the use of Kugelrohr distillation apparatus).

Herein divalent linking compounds are compounds that can link two components, such as two macrodiols or two macrodiamines, whereby the divalent compound is at the nexus between the two components. A divalent linking compound can create: urethane, urea, carbonate, amide, ester, and phosphonate linkages within the block copolymer segment.

Examples of divalent linking compounds are organophosphorus compounds or compounds comprising two functional groups, such as two: isocyanate, carboxylic acid or acid halide functional groups.

In one embodiment the divalent linking compound is a diisocyanate, for example: 1,4-diisocyanatobutane, 1,12-diisocyanatododecane, 1,6-diisocyantehexane, 1,8-diisocyanateoctane, 4,4'-methylenediphenyl diisocyanate (MDI), 4,4'-methylenebis(cyclohexyl diisocyanate) (H12MDI), p-phenylene diisocyanate (p-PDI), m-phenylene diisocyanate (m-PDI) trans-cyclohexane-1,4-diisocyanate (CHDI) or a mixture of the cis and trans isomers, 1,6-hexamethylene diisocyanate (HDI), 2,4-toluene diisocyanate (2,4-TDI) or its isomers (for example 2,6-toluene diisocyanate (2,6-TDI)), or mixtures thereof, p-tetramethylxylene diisocyanate (p-TMXDI), isophorone diisocyanate or m-tetramethylxylene diisocyanate (m-TMXDI), 1,5-diisocyanatonaphthalene (NDI), or a mixture thereof.

In another embodiment the divalent linking compound is an acid halide, for example phosgene.

In another embodiment the divalent compound is an organophosphorus compound, for example methylphosphonic dichloride.

Also disclosed herein is a process for preparing a thermoplastic polyurethane or polyurethaneurea elastomer comprising the silicon based block copolymer segment of Formula 1, whereby the process comprises the steps of:

i. providing a block copolymer segment of Formula 1 or preparing a block copolymer segment of Formula 1 using a process as described herein;
ii. optionally further reacting the material of step i. with a divalent compound and:
   a. at least one macrodiol;
   b. at least one macrodiamine; or
   c. a mixture of at least one macrodiol and at least one macrodiamine; and
iii. reacting the block copolymer segment of step i. or ii. with a chain extender or a mixture of chain extenders to form the polyurethane or polyurethaneurea elastomer.

Non-limiting examples of soft segments which could be produced for the thermoplastic polyurethane or polyurethaneurea elastomeric materials disclosed herein are shown in Schemes 1 to 4. In these schemes $R^{5a}$ and $R^{6a}$ are both $(CH_2)_2O(CH_2)_4$:

Scheme 1—The preparation of a linked macrodiol from poly(hexamethylene oxide) (PHMO) using 4,4'-methylenediphenyl diisocyanate (MDI) as the linker molecule.

Scheme 2—The preparation of a linked macrodiol from α,ω bis-(6-hydroxyethoxypropyl)polydimethylsiloxane (wherein $R^{5a}$ and $R^{6a}$ are ethoxypropyl groups) using MDI as the linker molecule.

Scheme 3—The preparation of a linked macrodiol from α,ω-bis-(6-hydroxyethoxypropyl)polydimethylsiloxane (wherein $R^{5a}$ and $R^{6a}$ are ethoxypropyl groups) using a carbonate linker:

Scheme 4—The preparation of a linked macrodiol from α,ω-bis-(6-hydroxyethoxypropyl)polydimethylsiloxane (wherein $R^{5a}$ and $R^{6a}$ are ethoxypropyl groups), using a phosphonate linker.

As a non-limiting example, Scheme 5 illustrates a possible reaction scheme and the general structure of the polyurethane urea prepared from MDI linked PHMO and PDMS chain extended with ethylene diamine.

Scheme 1

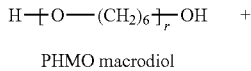

PHMO macrodiol

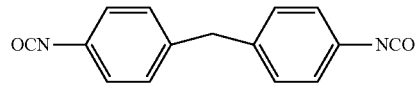

MDI

↓ 80° C./2 hrs

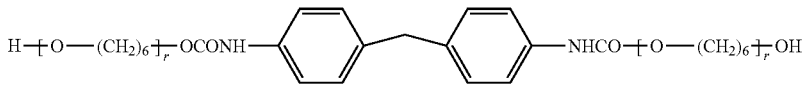

Scheme 2

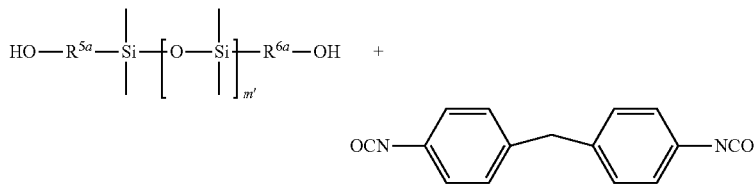

MDI

↓ 80° C./2 hrs

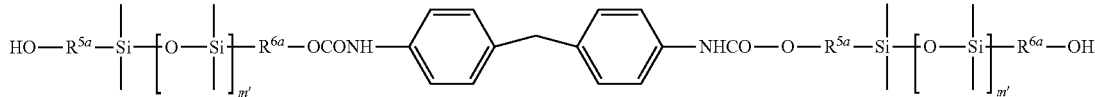

Scheme 3
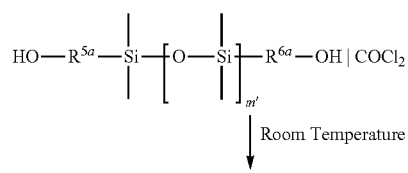
↓ Room Temperature
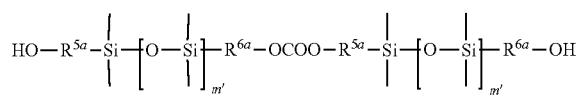
Scheme 4
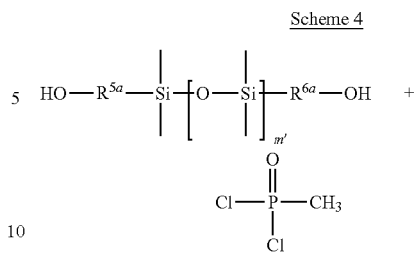
↓ Room Temperature
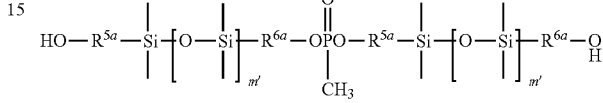
Scheme 5 operation 1
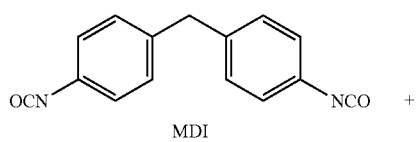
MDI +
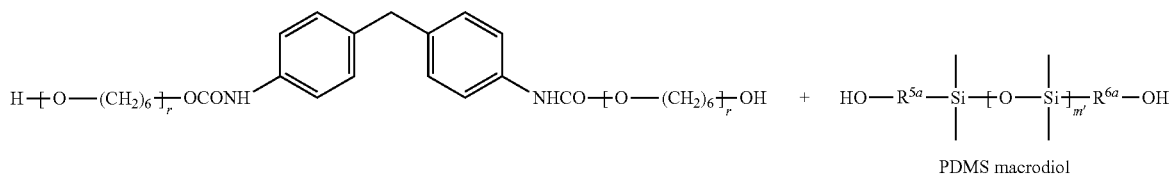
PDMS macrodiol
↓ 80° C./2h
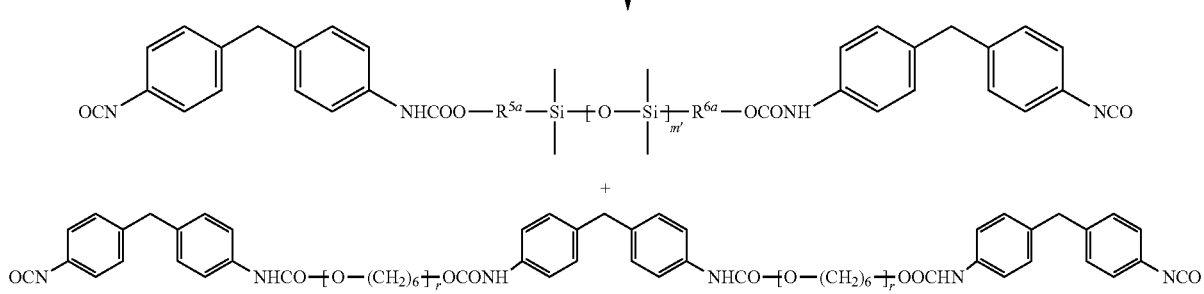
+
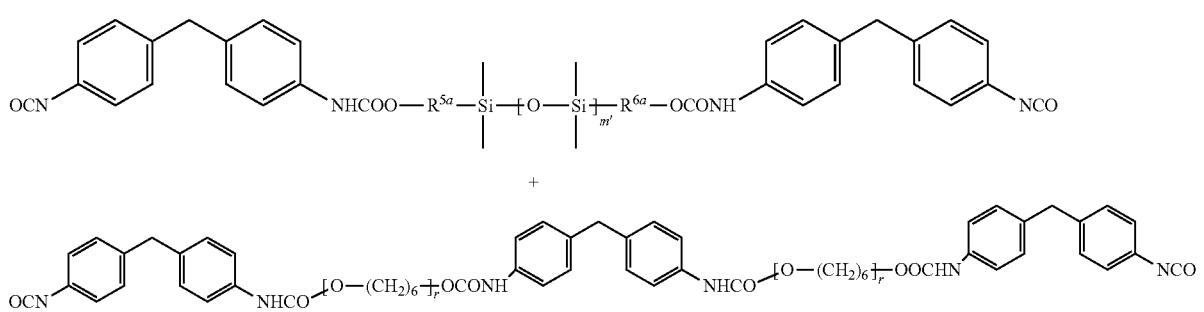
R = CH$_2$CH$_2$OCH$_2$CH$_2$CH$_2$CH$_2$
↓ Chain extender H$_2$NCH$_2$CH$_2$NH$_2$ -continued

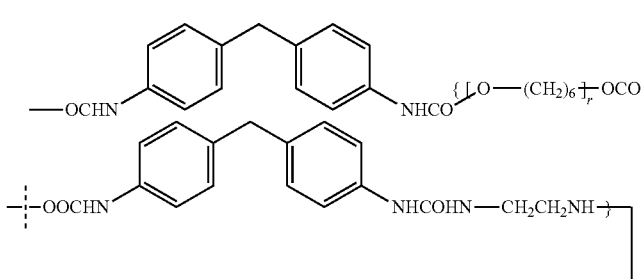

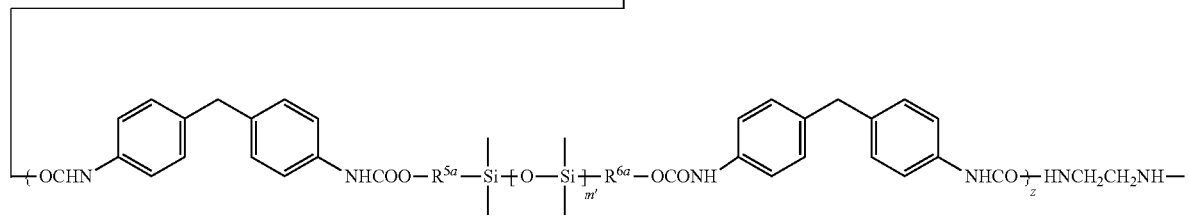

Materials and Articles

Disclosed herein are materials that comprise a thermoplastic polyurethane or polyurethaneurea elastomer material as defined herein.

The thermoplastic polyurethane or polyurethaneurea elastomer materials may be used to produce sheets of fabrics or fibres, especially for applications where materials possessing high tensile strength and/or tear strength are required. For example the thermoplastic polyurethane or polyurethaneurea elastomer materials can be used to produce fibres that may be used in knitting or weaving specialty fabrics, for example high strength and/or water-repellent membranes. In addition, the thermoplastic polyurethane or polyurethaneurea elastomer materials may be used as sealants. For materials comprising a siloxane component, due to the dielectric properties of said siloxane component, the thermoplastic polyurethane or polyurethaneurea elastomer materials may be used for electronic and electrical components and insulation.

Also disclosed herein are articles which are composed wholly or partly of a thermoplastic polyurethane or polyurethaneurea elastomer material as defined herein.

Examples of devices or articles include: artificial leather, shoe soles, cable sheathing, varnishes, coatings, structural components for pumps or vehicles, mining ore screens, conveyor belts, laminating compounds, fibres, textiles, separation membranes, sealants, and adhesive components.

Articles for Medical Applications

The thermoplastic polyurethane or polyurethaneurea elastomeric materials defined herein may be used as biomaterials. Herein, the term "biomaterial" is used in its broadest sense and refers to a material which is used in situations where it comes into contact with the cells and/or bodily fluids of living animals or humans.

Disclosed herein are articles which are medical devices which are composed wholly or partly of a thermoplastic polyurethane or polyurethaneurea elastomeric material as defined herein. In one embodiment the article which is a medical device is an implant.

Examples of medical devices include: a cardiac pacemaker, defibrillator, catheter, heart valve, cardiac assist device, vascular graft, implantable prosthesis, a cannula, extra-corporeal device, artificial organ, pacemaker lead, defibrillator lead, blood pump, balloon pump, A-V shunt, biosensor, membrane for cell encapsulation, drug delivery device, wound dressing, artificial joint, orthopaedic implant, or soft tissue replacement.

In one embodiment the article which is a medical device which is used in cardiovascular applications, for example an article that relates to one or more of the aortic, mitral, pulmonary, and/or tricuspid valves.

In another embodiment the article may be a heart valve, or similar product that can be inserted by a procedure called Transcatheter Aortic Valve Replacement (TAVI).

An example of an implantable valve 100 (for surgical and/or TAVI placement) is presented in FIG. 1. The valve includes a plurality of valve leaflets 110-1, 110-2, and 110-3 constructed from the subject polymers. Each of leaflets 110 can be discrete from the others (as shown) or can be portions of one unitary (monolithic) leaflet body. Support structure for the valve may include an annular base portion 102 that can have a planar or flat upstream terminus or can have a curved or scalloped upstream terminus (not shown) or extensions 104 that project from annular base portion 102 downstream relative to intended flow. The leaflets can be integrally formed on this base frame 102, such as through a casting (for example dip casting) or moulding process. In an example of a dip casting process, the base frame 102 is placed on a mandrel and dipped in a polymer, which results in the formation of leaflets integrated with a polymeric coating over the base frame. In some embodiments, leaflets 110 (formed of the subject polymers) can be physically joined to support structure 102 through a coupling process such as sewing.

Herein, the thermoplastic polyurethane or polyurethaneurea elastomeric materials used in the production of a medical device should be acceptable for use on or in a recipient, such as a human being. For example, the thermoplastic polyurethane or polyurethaneurea elastomeric material, should be able to contact tissues of a recipient without excessive toxicity, irritation, allergic response or other potential complications commensurate with a reasonable benefit/risk ratio identified by a skilled medical professional or veterinarian.

It will be appreciated that in some cases thermoplastic polyurethane or polyurethaneurea elastomeric materials as described herein may not be for use on or in a recipient, such as a human being, but can be useful in the preparation of thermoplastic polyurethane or polyurethaneurea elastomeric materials which could be utilised in the preparation of materials which are acceptable for use in medical devices.

The recipients of medical devices described herein can be human beings, male or female.

Alternatively the recipients of medical devices described herein can be a non-human animal. "Non-human animals" or "non-human animal" is directed to the kingdom Animalia, excluding humans, and includes both vertebrates and invertebrates, male or female, and comprises: warm blooded animals, including mammals (comprising but not limited to primates, dogs, cats, cattle, pigs, sheep, goats, rats, guinea pigs, horses, or other bovine, ovine, equine, canine, feline, rodent or murine species), birds, insects, reptiles, fish and amphibians.

The recipients of the medical devices described herein are referred herein with the interchangeable terms "patient", "recipient" "individual", and "subject". These four terms are used interchangeably and refer to any human or non-human animal (unless indicated otherwise), as defined herein.

EXAMPLES

Raw Materials

Certain chemicals referred to within the specification, including the following examples, can be obtained from the suppliers indicted in Table 2.

TABLE 2

Suppliers for selected compounds disclosed in the examples.

| Component | Example Supplier |
| --- | --- |
| α,ω Bis-(6-hydroxyethoxypropyl)polydimethylsiloxane (molecular weight 928) | Shin-Etsu |
| Hydrogenated poly(butadiene) diol | Kraysol ® from Cray Valley |
| 4,4'-methylene diphenyl diisocyanate | BASF |
| 1,4-Butanediol | Aldrich |
| 1,3 bis-(3-aminopropyl) tetramethyldisiloxane | Shin-Etsu |
| 1,1,3,3-Bis-hydroxybutyl tetramethyl disiloxane | Shin-Etsu |

Equipment

Gel Permeation Chromatography: Waters THF System

Gel permeation chromatography (GPC) was performed on a Waters Alliance system equipped with an Alliance 2695 Separations Module (integrated quaternary solvent delivery, solvent degasser and autosampler system), a Waters column heater module, a Waters 2414 RDI refractive index detector, a Waters PDA 2996 photodiode array detector (210 to 400 nm at 1.2 nm) and 4× Agilent PL-Gel columns (3×PL-Gel Mixed C (5 µm) and 1×PL-Gel Mixed E (3 µm) columns), each 300 mm×7.8 mm$^2$, providing an effective molar mass range of 10 to 4×10$^5$). Tetrahydrofuran (THF) high purity solvent (HPLC grade) was pre-filtered through aluminium oxide (90 active neutral, 70-230 mesh) with 0.45 µm filter, and 0.1 g L$^{-1}$ 2,6-di-tert-butyl-4-methylphenol (BHT) was added as inhibitor. The filtered THE containing BHT was purged slowly with nitrogen gas and used as an eluent with a flow rate of 1 mL/min at 30° C. Number ($M_n$) and weight average ($M_w$) molar masses were evaluated using Waters Empower-3 software. The GPC columns were calibrated with low dispersity polystyrene (PSt) standards (Polymer Laboratories) ranging from 265 to 2,560,000 g mol$^{-1}$, and molar masses are reported as PSt equivalents. A 3$^{rd}$-order polynomial was used to fit the log $M_p$ vs. time calibration curve, which was near linear across the molar mass ranges.

Gel Permeation Chromatography: Shimadzu-DMAc

Gel permeation chromatography (GPC) was performed on a Shimadzu system equipped with a CMB-20A controller system, an SIL-20A HT autosampler, an LC-20AT tandem pump system, a DGU-20A degasser unit, a CTO-20AC column oven, an RDI-10A refractive index detector, and 4×Waters Styragel columns (HT2, HT3, HT4, and HT5, each 300 mm×7.8 mm$^2$, providing an effective molar mass range of 100-4×10$^6$). N,N-Dimethylacetamide (DMAc) (containing 4.34 g L$^{-1}$ lithium bromide (LiBr)) was used as an eluent with a flow rate of 1 mL/min at 80° C. Number ($M_n$) and weight average ($M_w$) molar masses were evaluated using Shimadzu LC Solution software. The GPC columns were calibrated with low dispersity polystyrene (PSt) standards (Polymer Laboratories) ranging from 575 to 3,242,000 g mol$^{-1}$, and molar masses are reported as PSt equivalents. A 3$^{rd}$-order polynomial was used to fit the log $M_p$ vs. time calibration curve, which was near linear across the molar mass ranges Film preparation by solvent casting and testing of mechanical properties: Polymer films of 80 mm×145 mm size were prepared by placing a solution of the polymer in a Teflon mould and then evaporating the solvent slowly in a nitrogen circulating oven at 60° C. for few hours followed by further drying under a vacuum (1 torr) overnight. The films were then equilibrated at room temperature for at least 24 hours before using them for tensile property measurement.

Dumbbell shaped specimens of polymer film were punched using a die and a manual cutting Press (IDM Instruments). The specimens had dimensions of 75 mm length, 13 mm width at each end and 4 mm at the central narrow section (constant width over at least 15 mm of length). Thickness of the cut out specimen was measured using a digital thickness gauge (Mitutoyo, Japan). In case there was small variation in thickness over the length of 15 mm in the central narrow section, an average of three thickness values was taken. Instron 5565 fitted with static load cell ±100 N was initialized and the load was calibrated using Instron Bluehill 2 (version 2.35) software. For the tensile test at dry condition, the specimen was fixed between upper and lower grips (Instron) such that the gap between the grips was 10 mm. The 10 mm long section of the film was stretched at the rate of 50 mm per minute until the film broke. At least three replicates of specimen were tested for each film. In case of wide discrepancy between results, five tests were carried out. Stress, strain, breaking stress and elongation at breaking were obtained from the software. These parameters allow one to obtain values for the tensile strength, the Young's modulus (stiffness) and Elongation (elasticity) of the samples.

For the tensile test at wet condition, (or replication of conditions found in medical applications) the cut out specimen of known thickness was put in a plastic bag and immersed in water maintained at 37° C. for at least two hours. The specimen was quickly dried using tissue paper and fixed between the grips and stretched at the rate of 100 mm per min until the film broke. Stress, strain, breaking stress and elongation at breaking were obtained from the software. The stress values were plotted against strain (% of initial value).

Abbreviated Terms

Table 3 lists a series of abbreviated terms which are used herein.

TABLE 3

Acronyms used for compounds and components described herein

| Acronym | Compound/Component |
| --- | --- |
| BAPD | 1,3 Bis-(3-aminopropyl) tetramethyldisiloxane |
| DMAc | N'N-Dimethylacetamide |
| GPC | Gel Permeation Chromatography |
| MDI | 4,4'-Methylenediphenyldiisocyanate |
| $M_n$ | Number Average Molecular Weight |
| $M_w$ | Weight Average Molecular Weight |
| PDI | Polydispersity Index |
| PDMS | α,ω Bis-(6-hydroxyethoxypropyl)polydimethylsiloxane |
| PHMO | Poly(hexamethylene oxide) |
| PU | Polyurethane |
| PUU | Polyurethaneurea |
| EDA | 1,2-ethanediamine |
| BDO | 1,4-butanediol |
| BHTD | 1,1,3,3-bis-hydroxybutyltetramethylene disiloxane |

Example 1—Synthesis of Urethane Linked Poly(hexamethylene oxide) (PHMO-u-PHMO)

Poly(hexamethylene oxide) (PHMO) (molecular weight 696.23) was prepared according to a method described in: P. A. Gunatillake, G. F. Meijs, R. C. Chatellier, D. M. McIntosh and E. Rizzardo, *Polym. Int.*, 7, 275-283, 1992; and
U.S. Pat. No. 5,403,912.

The PHMO was dried and degassed by heating at 105° C. for about 15 hours under vacuum (0.1 torr) until the moisture content was below 200 ppm, as determined by Karl Fisher titration. All glassware used were dried overnight at 105° C. prior to use in the experiment. Accurately weighed molten 4,4'-methylenediphenyldiisocyanate (MDI) (7.18 g) was placed in a round bottom flask equipped with: a mechanical stirrer, addition funnel and a nitrogen inlet. The flask was then placed in an oil batch at 80° C. Pre-dried PHMO (40.00 g) was weighed and added to MDI with stirring over a period of 20 minutes. The reaction mixture was further reacted for about 2 hours until all the isocyanate was consumed. This was confirmed by the absence of an IR absorption band at 2275 cm$^{-1}$.

Characterisation data for the PHMO prior to and after linking is shown in Table 4.

TABLE 4

Molecular Weight Characterisation Data for Example 1:

| System | $M_n$ | $M_w$ | PDI |
| --- | --- | --- | --- |
| PHMO-Before Linking | 1333 | 1999 | 1.49 |
| PHMO-After Linking (Urethane) | 4322 | 7272 | 1.68 |

The linked-PHMO was stored under nitrogen at ambient temperature until further use.

Example 2 Synthesis of Urethane Linked α,ω-Bis-(6-hydroxyethoxypropyl)polydimethylsiloxane (PDMS-u-PDMS)

α,ω-Bis-(6-hydroxyethoxypropyl)polydimethylsiloxane (molecular weight 928) was dried and degassed at 105° C. for about 15 hours until the moisture content was below 200 ppm as determined by Karl Fisher titration. All glassware used were dried overnight at 105° C. before use in the experiment. Accurately weighed molten MDI (6.74 g) was placed in a round bottom flask equipped with: a mechanical stirrer, addition funnel and a nitrogen inlet. The flask was then placed in an oil batch at 80° C. Pre-dried PDMS (50.0 g) was weighed accurately and added to MDI with stirring over a period of 20 minutes. The reaction mixture was further reacted with stirring at 80° C. for about 2 hours until all the isocyanate was consumed, which was confirmed by the absence of an IR absorption band at 2275 cm$^{-1}$.

Characterisation data for the PHMO prior to and after linking is shown in Table 5.

TABLE 5

Molecular Weight Characterisation Data for Example 2:

| System | $M_n$ | $M_w$ | PDI ($=M_w/M_n$) |
| --- | --- | --- | --- |
| Siloxane-Before Linking | 1334 | 1475 | 1.30 |
| Siloxane-After Linking (Urethane) | 5302 | 7468 | 1.40 |

The results showed that the linking reaction was successful. Following the reactions, the product was stored under nitrogen at ambient temperature.

Example 3—Synthesis of the Carbonate Linked PDMS (PDMS-c-PDMS)

In a three-necked 1 L round bottomed flask equipped with: a silica gel drying tube, a 250 mL pressure compensating dropping funnel, a thermometer, and a magnetic stirrer bar, were placed 200 ml of dry toluene and 49.48 g of a 20% solution of phosgene in toluene. The flask was cooled, whilst stirring, to 0° C. 23.62 g of pyridine was added dropwise to the mixture from the dropping funnel. The addition was made over a 15 minute period during which time the temperature was maintained in the range 0-5° C. 270.82 g of α,ω-bis(hydroxyethoxypropyl) polydimethylsiloxane (molecular weight 928) was then added drop wise to the mixture from the dropping funnel. The addition was made over a 1 hour period during which time the temperature of the mixture rose to 15° C. after which the reaction mixture was maintained at 15° C. for 2 hours. During this period pyridine hydrochloride precipitated out of the reaction mixture. The reaction mixture was filtered through celite to remove the pyridine hydrochloride. The toluene was removed by rotary evaporator at 80° C. under a reduced pressure of 20 torr. The mixture was transferred to a Kugelrohr distillation apparatus and stripped of low molecular weight species at 150° C. under a reduced of 8×10$^{-2}$ torr to give 202 g of (PDMS-1000)-c-(PDMS-1000) as a colourless oil (molecular weight 1924).

Example 4—Synthesis of the Phosphate Linked PDMS (PDMS-p-PDMS)

In a 500 ml round bottomed flask equipped with a magnetic stirrer bar were placed 100 ml of dry ether, 69.82 g of α,ω-bis(hydroxyethoxypropyl) polydimethylsiloxane (molecular weight 928), and 7.61 g of triethylamine. A solution of 23.62 g of methylphosphonic dichloride in 50 ml of ether was added drop wise to the mixture from the dropping funnel. During this period triethylamine hydrochloride precipitated out of the reaction mixture. The reaction was stirred for a further 3 days at room temperature. The reaction mixture was filtered to remove the pyridine hydrochloride. The ether was removed by rotary evaporator at 80° C. under a reduced pressure of 20 torr to give 72 g of PDMS-1000-P(O)Me-PDMS as a colourless oil.

Example 5—Preparation of a Polyurethaneurea (PUU) Using Linked PHMO-u-PHMO, PDMS, BAPD with 40 Hard Segment Percentage Accurately weighed linked PHMO-u-PHMO (10.00 g) prepared according to the method described in Example 1, and α,ω-bis(hydroxyethoxypropyl) polydimethylsiloxane (PDMS) (MW 973, 40.00 g) were mixed in a flask and degassed at 80° C. under vacuum (0.1 torr) for 2 hours. MDI (22.94 g) was accurately weighed in to a round bottom flask equipped with: a mechanical stirrer, addition funnel and a nitrogen inlet. The flask was then placed in an oil batch at 80° C. The mixture of PHMO-u-PHMO and PDMS was added slowly over period of 30 minutes using an addition funnel to with stirring to MDI in the flask. After the addition was over, the reaction mixture was heated at 80° C. for 2 hours with stirring under nitrogen. Anhydrous N'N-dimethylacetamide (DMAc, 500 mL) was then added using a syringe to the reaction mixture and stirred for 5 minutes until a clear solution is obtained. The solution was cooled in an ice bath to 0° C. and 1,3bis-(3-aminopropyl) tetramethyldisiloxane (BAPD, 10.40 g) dissolved in anhydrous DMAc (25 mL) was added dropwise to the pre-polymer solution in the flask with stirring. After the addition was over, the polymer solution was heated to 90° C. for a period of 3 hours and transferred into a Schott bottle.

The polymer solution, after allowing to degas, was cast as thin film by pouring on to a Teflon mould. The mould was placed in an oven under a slow stream of nitrogen at 60° C. for 6 hours to remove the solvent, followed by placing it under vacuum (0.1 torr) for a further 16 hours to remove any remaining solvent.

Characterisation data for the prepared polymer is shown in Table 6.

Example 6—Preparation of a Polyurethaneurea (PUU) Using Linked PDMS-u-PDMS, PHMO, BAPD with 40 Hard Segment Percentage Accurately weighed linked PDMS-u-PDMS (40.00 g) prepared according to the method described in Example 2, and PHMO (MW 696, 10.00 g) were mixed in a flask and degassed at 80° C. under vacuum (0.1 torr) for 2 hours. MDI (21.19 g) was accurately weighed in to a round bottom flask equipped with: a mechanical stirrer, addition funnel and a nitrogen inlet. The flask was then placed in an oil batch at 80° C. The mixture of PDMS-u-PDMS and PHMO was added slowly over period of 30 minutes using an addition funnel to with stirring to MDI in the flask. After the addition was over, the reaction mixture was heated at 80° C. for 2 hours with stirring under nitrogen. Anhydrous DMAc (500 ml) was then added using a syringe to the reaction mixture and then stirred for 5 minutes until a clear solution was obtained. The solution was cooled in an ice bath to 0° C. and BAPD (12.14 g) dissolved in anhydrous DMAc (25 mL) was added dropwise to the pre-polymer solution in the flask with stirring. After the addition was over, the polymer solution was heated to 90° C. for a period of 3 hours and transferred into a Schott bottle.

The polymer solution, after allowing to degas, was cast as thin film by pouring on to Teflon mould. The mould was placed in an oven under a slow stream of nitrogen at 60° C. for 6 hours to remove the solvent, followed by placing the mould under vacuum (0.1 torr) for 16 hours to remove any remaining solvent.

Characterisation data for the prepared polymer is shown in Table 6.

Example 7—Preparation of a Polyurethaneurea (PUU) Using Linked PDMS-c-PDMS, PHMO, BAPD with 40 Hard Segment Percentage Accurately weighed linked PDMS-c-PDMS (40.00 g) prepared according to the method described in Example 2, and PHMO (molecular weight 696, 10.00 g) were mixed in a flask and degassed at 80° C. under vacuum (0.1 torr) for 2 hours. MDI (21.42 g) was accurately weighed in to a round bottom flask equipped with: a mechanical stirrer, addition funnel and a nitrogen inlet. The flask was then placed in an oil batch at 80° C. The mixture of PDMS-c-PDMS and PHMO was added slowly over period of 30 minutes using an addition funnel to with stirring to MDI in the flask. After the addition was over, the reaction mixture was heated at 80° C. for 2 hours with stirring under nitrogen. Anhydrous DMAc (500 mL) was then added using a syringe to the reaction mixture and stirred for 5 minutes until a clear solution was obtained. The solution was cooled in an ice bath to 0° C. and BAPD (11.91 g) dissolved in anhydrous DMAc (25 mL) was added dropwise to the pre-polymer solution in the flask with stirring. After the addition was over, the polymer solution was heated to 90° C. for a period of 3 hours and transferred into a Schott bottle.

The polymer solution, after allowing to degas, was cast as thin film by pouring on to Teflon mould. The mould was placed in an oven under a slow stream of nitrogen at 60° C. for 6 hours to remove DMAc, followed by under vacuum (0.1 torr) for 16 hours to remove any remaining solvent.

Characterisation data for the prepared polymer is shown in Table 6.

Example 8—Preparation of a Polyurethaneurea (PUU) Using Linked PDMS-u-PDMS and BAPD without PHMO with 40 Hard Segment Percentage Accurately weighed linked PDMS (40.0 g) was degassed at 80° C. for 2 hours under vacuum (0.1 torr). Molten MDI (15.88 g) was placed in a three necked flask equipped with: a mechanical stirrer, dropping funnel and a nitrogen inlet. The flask was then placed in an oil bath at 70° C. The degassed macrodiol mixture (50 g) was added dropwise through the addition funnel over a period of 30 minutes. After the addition was over, the reaction mixture was heated at 80° C. for 2 hours with stirring under nitrogen. Anhydrous DMAc (500 mL) was then added through a syringe to the reaction mixture and stirred for 5 minutes until it was a clear solution. The solution was then cooled in an ice bath to 0° C. and BAPD (10.79 g) mixed with anhydrous DMAc (50 mL) was added dropwise into the above solution. After the addition was over, the above polymer solution was heated to 90° C. for a period of 3 hours and transferred into a Schott bottle. The polymer solution was then degassed at 60° C. in a nitrogen circulating oven and cast into a 0.5-mm thick film.

The polymer solution, after allowing to degas, was cast as thin film by pouring on to Teflon mould. The mould was placed in an oven under a slow stream of nitrogen at 60° C. for 6 hours to remove solvent. The mould was then placed under vacuum (0.1 torr) for 16 hours to remove any remaining solvent.

Example 9—Preparation of a Polyurethaneurea (PUU) Using Linked PDMS-c-PDMSO, BDO with 40 Hard Segment Percentage by One-Step Bulk Polymerisation A mixture of pre-dried linked PDMS-c-PDMS (20.0 g) and 1,4-butanediol (BDO) (2.85 g) was weighed in a PP beaker and degassed at 80° C. under a vacuum of 0.1 torr for over an hour. The vacuum was released under nitrogen and dibutyltindilaurate (DBTL) catalyst 0.1 wt-% was added and stirred manually with the spatula. Molten MDI (10.49 g) was then added to the reaction mixture at once and stirred rapidly using spatula until viscous enough and then poured into Teflon tray and cured at 100° C. for 18 hours. The polymer was then compression moulded into a film using hot press at 180° C. for mechanical properties.

Example 10—Preparation of a Polyurethaneurea (PUU) Using Linked PHMO-u-PHMO, PDMS, BAPD with 50 Hard Segment Percentage A PUU was synthesised according procedure as described in Example 5. The following quantities of reagents were used:
linked PHMO-u-PHMO (10.0 g);
PDMS (40.0 g);
MDI (31.68 g); and
BAPD (18.32 g).
Characterisation data for the prepared PUU is shown in Table 6.

Example 11—Preparation of a Polyurethaneurea (PUU) Using Linked PHMO-u-PHMO, PDMS, EDA with 50 Hard Segment Percentage The PUU was synthesised according procedure as described in Example 5. The following quantities of reagents were used:
linked PHMO-u-PHMO (10.0 g);
PDMS (40.0 g);
MDI (42.94 g); and
EDA (7.06) g.
Characterisation data for the prepared PUU is shown in Table 6.

Example 12—Preparation of a Polyurethaneurea (PUU) Using Linked PDMS-u-PDMS, PHMO, BAPD with 50 Hard Segment Percentage A PUU was synthesised according to the procedure as described in Example 5. The following quantities of reagents were used:
linked PDMS-u-PDMS (40.0 g);
PHMO (10.0 g);
MDI (29.39 g); and
BAPD (20.61 g).
Characterisation data for the prepared PUU is shown in Table 6.

Example 13—Preparation of a Polyurethaneurea (PUU) Using Linked PHMO-u-PHMO, PDMS, BAPD:EDA (8:2) with 50 Hard Segment Percentage A mixture of PDMS (40.0 g) and PHMO-u-PHMO (10.0 g) was degassed at 80° C. for 2 hours under vacuum (0.1 torr). Molten MDI (32.91 g) was placed in a three necked flask equipped with: a mechanical stirrer, dropping funnel and a nitrogen inlet. The flask was then placed in an oil bath at 70° C. The degassed macrodiol mixture (50 g) was added dropwise through the addition funnel over a period of 30 minutes. After the addition was over, the reaction mixture was heated at 80° C. for 2 hours with stirring under nitrogen. Anhydrous DMAc (500 mL) was then added through a syringe to the reaction mixture and stirred for 5 minutes until it was a clear solution. The solution was then cooled in an ice bath to 0° C. BAPD (16.11 g) mixed with ethylene diamine (0.97 g) dissolved in anhydrous DMAc (60 mL) was added dropwise into above solution. After the addition was over, the above polymer solution was heated to 90° C. for a period of 3 hours and transferred into a Schott bottle. The polymer solution was then degassed at 60° C. in a nitrogen circulating oven and cast into a thin film as described in Example 5.

Characterisation data for the prepared PUU is shown in Table 6.

Example 14—Preparation of a Polyurethaneurea (PUU) Using Linked PHMO-u-PHMO, PDMS, BHTD:EDA (6:4) with 45 Hard Segment Percentage A mixture of PDMS (40.0 g) and PHMO-u-PHMO (10.0 g) was degassed at 80° C. for 2 hours under vacuum (0.1 torr). Molten MDI (28.65 g) was placed in a three necked flask equipped with: a mechanical stirrer, dropping funnel and a nitrogen inlet. The flask was then placed in an oil bath at 70° C. The degassed macrodiol mixture (50.0 g) was added through the addition funnel over a period of 30 minutes. After the addition was over, the reaction mixture was heated at 80° C. for 2 hours with stirring under nitrogen. 1,1,3,3-Bis-hydroxybutyltetramethylene disiloxane (BHTD) (10.72 g) was then added to the reaction mixture and the system was allowed to react for a further 2 hours. The reaction mixture was then cooled down to 0° C. and anhydrous DMAc (500 mL) was then added through a syringe to the reaction mixture and stirred for 5 minutes until it was a clear solution. EDA (1.54 g) dissolved in anhydrous DMAc (60 mL) was added dropwise into above solution. After the addition was over, the above polymer solution was heated to 90° C. for a period of 3 hours and then transferred into a Schott bottle. The polymer solution was then degassed at 60° C. in a nitrogen circulating oven and cast into a thin film as described in Example 5.

Characterisation data for the prepared PUU is shown in Table 6.

Example 15—Preparation of a Polyurethaneurea (PUU) Using Linked PHMO-u-PHMO, PDMS, BHTD:EDA (4:6) with 45 Hard Segment Percentage The PUU was synthesised according to the procedure described in Example 14. The following quantities of reagents were used:
linked PHMO-u-PHMO (10.0 g);
PDMS (40.0 g);
MDI (30.42 g);
BHTD (7.93 g); and
EDA (2.57 g).
Characterisation data for the prepared PUU is shown in Table 6.

Example 16—Preparation of a Polyurethaneurea (PUU) Using Linked PHMO-u-PHMO, PDMS, BDO:EDA (6:4) with 45 Hard Segment Percentage The PUU was synthesised according to the procedure described in Example 14. The following quantities of reagents were used:
linked PHMO-u-PHMO (10.0 g);
PDMS (40.0 g);
MDI (34.19 g);
BHTD (4.65 g); and
BDO (2.07 g).
Characterisation data for the prepared PUU is shown in Table 6.

Example 17—Preparation of a Polyurethaneurea (PUU) Using Linked PDMS-u-PDMS, PHMO, BHTD:EDA (6:4) with 45 Hard Segment Percentage The PUU was synthesised following procedure as described in Example 14. The amount of precursors used are as follows:
linked PHMO-u-PHMO (10.0 g);
PDMS (40.0 g);
MDI (26.92 g);
BHTD (12.23 g); and
EDA (1.76 g).
Characterisation data for the prepared PUU is shown in Table 6.

Example 18—Preparation of a Polyurethaneurea (PUU) Using Linked PDMS-u-PDMS, PHMO-u-PHMO, BHTD:EDA (6:4) with 45 Hard Segment Percentage The PUU was synthesised according to the procedure described in Example 14. The following quantities of reagents were used:
linked PHMO-u-PHMO (10.0 g);
PDMS-u-PDMS (40.0 g);
MDI (26.02 g);
BHTD (13.02 g); and
EDA (1.87 g).
Characterisation data for the prepared PUU is shown in Table 6.

Example 19—Preparation of a Polyurethaneurea (PUU) Using Linked PHMO-u-PHMO, PDMS, BHTD:EDA (50:50) with 45 Hard Segment Weight Percentage The PUU was synthesised according to the procedure described in Example 14. The following quantities of reagents were used:
linked PHMO-u-PHMO (20.0 g);
PDMS (80.0 g);
MDI (58.33 g);
BHTD (19.32 g); and
EDA (4.17 g).

Example 20—Preparation of a Polyurethaneurea (PUU) Using Linked PHMO-u-PHMO, PDMS, BAPD with 40 Hard Segment Weight Percentage The PUU was synthesised according to the procedure described in Example 14. The following quantities of reagents were used:
linked PHMO-u-PHMO (10.0 g);
PDMS (40.0 g);
MDI (29.32 g); and
BAPD (4.02 g).

Example 21—Tensile Testing of the Materials Produced in Examples 5-7, 10 & 12-20

Tensile testing was carried out using dumbbells punched from dried polyurethaneurea films prepared in Examples 5 to 7, 10 and 12-20. Tensile testing was carried out on an Instron model 5565 Universal Testing Machine. The results are summarised in Table 6. These results indicate that the polyurethaneurea polymers of the current invention demonstrate high tensile strength and high elongation compared to polyurethaneurea polymers in the prior art.

Tensile testing of films prepared in Examples 13, 17, 18 and 20 was carried out on an Instron model 5565 Universal Testing Machine using the procedure described under the heading "Equipment".

Characterisation data for the prepared PUUs are shown in Table 6 and Table 7.

TABLE 6

The molecular weight and tensile properties of polyurethaneureas prepared as described in Examples 5-7, 10 and 12-20 measured at ambient temperature.

| Example | Ultimate Tensile Strength (MPa) | Young's Modulus (MPa) | Elongation at Break (%) | GPC Data | | |
|---|---|---|---|---|---|---|
| | | | | $M_n$ | Mw | PDI |
| 5 | 20.6 ± 2.5 | 11.20 ± 0.8 | 1871 ± 26 | 85762 | 192726 | 2.2 |
| 6 | 22.26 ± 1.7 | 16.6 ± 0.7 | 1361 ± 12 | 86486 | 208711 | 2.35 |
| 7 | 6.0 ± 0.8 | 20.7 ± 4.0 | 570 ± 20 | 69106 | 214173 | 2.8 |
| 10 | 14.98 ± 6.3 | 16.6 ± 0.7 | 1361 ± 12 | 72816 | 142744 | 1.94 |
| 12 | 20.6 ± 2.5 | 11.20 ± 0.8 | 1871 ± 26 | 85762 | 192726 | 2.2 |
| 13 | 28.47 ± 1.5 | 57.7 ± 2.6 | 830 ± 4.9 | 119896 | 351073 | 2.53 |
| 14 | 18.5 ± 3.2 | 21.6 ± 3.0 | 1170 ± 13 | 143469 | 544021 | 2.73 |
| 15 | 36.8 ± 0.8 | 52.8 ± 0.5 | 1100 ± 30 | 129302 | 272731 | 2.01 |
| 16 | 31.7 ± 0.3 | 66.2 ± 6.1 | 860 ± 84 | 82800 | 156265 | 1.83 |
| 17 | 26.6 ± 13.4 | 39.28 ± 8.5 | 990 ± 36 | 123109 | 394717 | 2.65 |
| 18 | 36.7 ± 3.6 | 35.1 ± 1.8 | 1180 ± 11 | 104911 | 213576 | 1.95 |
| 19 | 34.0 ± 2.7 | 35.8 ± 2.1 | 1367 ± 42 | 89147 | 253274 | 2.84 |
| 20 | 23.6 ± 2.4 | 67.97 ± 10.9 | 800 ± 12 | 87372 | 158008 | 1.73 |

TABLE 7

The tensile properties of polyurethaneureas prepared as described in Examples 13, 17, 18, and 20 measured at 37° C. temperature.

| Example | Ultimate Tensile Strength (MPa) | Young's Modulus (MPa) | Elongation at Break (%) |
|---|---|---|---|
| 13 | 27.53 ± 2.8 | 29.44 ± 0.63 | 950 ± 3 |
| 17 | 22.96 ± 10.64 | 37.09 ± 4.8 | 860 ± 25 |
| 18 | 30.55 ± 3.2 | 28.84 ± 0.59 | 1180 ± 11 |
| 20 | 23.06 ± 2.3 | 56.49 ± 4.2 | 880 ± 5 |

The polyurethaneureas prepared according to the present invention exhibit high tensile strength, low modulus and high elongation as shown in Table 6. In particular, the polyurethaneureas prepared according to Examples 15 and 16 had tensile strength exceeding 30 MPa with elongation at break over 1000%. This combination of properties is unique and far exceeded those reported in prior art. For example, the polyurethaneureas disclosed in International Patent Application WO00/64971 had elongations at break less than 500% for materials described in all Examples.

Example 22: Preparation of Polyurethaneureas Using Linked-PHMO and Linked PDMS Synthesized from Different Diisocyanates Diisocyanates MDI, 1,6 hexamethylene diisocyanate (HDI) and isophorone diisocyanate (IPDI) were used as linker dioscyanates in preparing series of PUUs in this Example.

PHMO and PDMS were purified as described in Example 1 and 2, respectively. Chain extenders 1,2 ethylenediamine (EDA) and 1,3-bis(4-hydroxybutyl)-1,1,3,3-tetramethyldisiloxane (BHTD), received respectively from Aldrich and Silar Lab were used as received.

Preparation of Linked Macrodiols:

100.0 g of pre-dried PHMO (molecular weigh 713 g. $mol^{-1}$) was placed in a three-neck round-bottom flask equipped with a magnetic stirrer and a nitrogen inlet. The flask was placed in an oil bath at 80° C. 17.53 g of molten MDI (molecular weight 250.25 g·$mol^{-1}$) was placed in an addition funnel and added to PHMO while stirring within one minute. The reaction mixture was further reacted for two hours and the completion of the reaction was monitored using Fourier transform infrared (FTIR) spectroscopy.

Similarly, PDMS (molecular weight 998 g·$mol^{-1}$) was linked with MDI. A similar procedure was followed to link PHMO and PDMS with HDI and IPDI separately. Amounts of the compounds used for each macrodiol coupling is tabulated in Table 8. All the linked macrodiols were degassed at 80° C. under vacuum (0.1 torr) for 15 hours prior to use in experiments. Molecular weights were determined by the hydroxyl number determination and were in agreement with the theoretical values.

TABLE 8

Weight of macrodiol and diisocyanate used in preparing linked-macrodiols

| Linked-Macrodiol | Weight/g | |
|---|---|---|
| | Macrodiol | Diisocyanate |
| PHMO-MDI-PHMO | 100 | 17.53 |
| PDMS-MDI-PDMS | 150 | 18.80 |
| PHMO-HDI-PHMO | 100 | 11.54 |
| PDMS-HDI-PDMS | 100 | 8.42 |
| PHMO-IPDI-PHMO | 100 | 15.24 |
| PDMS-IPDI-PDMS | 100 | 11.13 |

Preparation of Polyurethenureas

Molten MDI (7.29 g) was weighed into a three-neck round-bottom flask equipped with a mechanical stirrer and nitrogen inlet. The flask was place in an oil bath at 70° C. A mixture of pre-dried linked PHMO-MDI-PHMO (2.5 g) and PDMS (10.0 g) was quickly added to MDI using an addition funnel while stirring. After the addition was complete the reaction mixture was heated up to 80° C. and allowed to react for 2 hours with continuous stirring under nitrogen.

Prepared pre-polymer was first chain extended with 2.4154 g of BHTD by slowly adding to the pre-polymer using a syringe and allowed to react for 2 hours while stirring under nitrogen. The reaction mixture was cooled down to 0° C. and 178 mL of anhydrous DMAc was added to get a clear solution. $5.212 \times 10^{-1}$ g of EDA in 3 mL of DMAc was added dropwise using a syringe into the cooled BHTD chain extended reaction mixture with slow stirring. After complete addition of EDA, the mixture was further reacted for 30 minutes to complete the reaction. When the solution viscosity increased, the stirring was stopped and the reaction mixture was heated up to 80° C., the system was then stirred until the solution turned clear. Prepared PUU was transferred to a screw-capped glass bottle under nitrogen and stored at room temperature.

A similar procedure was followed to synthesise PUUs with all other linked macrodiols.

Table 9 shows the material of the PUUs prepared along with sample abbreviation.

TABLE 9

Sample abbreviation and quantities of reagents used in preparing each of the polyurethaneureas

| Sample Abbreviation | PDMS or Linked PDMS[a] | PHMO or Linked PHMO[b] | MDI | BHTD | EDA |
|---|---|---|---|---|---|
| PU-C | PDMS | PHMO | 7.49 | 2.25 | 0.4863 |
| PU-1 | PDMS | PHMO-MDI-PHMO | 7.29 | 2.41 | 0.5212 |
| PU-2 | PDMS-MDI-PDMS | PHMO | 6.97 | 2.68 | 0.5775 |
| PU-3 | PDMS | PHMO-HDI-PHMO | 7.30 | 2.41 | 0.5199 |
| PU-4 | PDMS-HDI-PDMS | PHMO | 6.94 | 2.70 | 0.5825 |
| PU-5 | PDMS | PHMO-IPDI-PHMO | 7.29 | 2.42 | 0.5212 |
| PU-6 | PDMS-IPDI-PDMS | PHMO | 6.93 | 2.71 | 0.5854 |

[a]Amount used was 10.00 g; [b]amount used was 2.5 g

The molecular weight of synthesised polyurethanesureas was determined by gel permeation chromatography using procedures described under the heading "Equipment" and the results are summarized in Table 10.

TABLE 10

GPC molecular weights of synthesised poly(urethane-urea)

| Sample code | $M_n$ | $M_w$ | $M_w/M_n$ (PDI) |
|---|---|---|---|
| PU-C | 100813 | 328694 | 3.26 |
| PU-1 | 124147 | 314206 | 2.53 |
| PU-2 | 91048 | 245414 | 2.69 |
| PU-3 | 90471 | 260001 | 2.87 |
| PU-4 | 99649 | 355041 | 3.56 |
| PU-5 | 113923 | 347978 | 3.05 |
| PU-6 | 109531 | 262741 | 2.39 |

Example 23—Tensile Testing of Materials Prepared in Example 22

Tensile testing was carried out using dumbbells punched from dried polyurethaneurea films cast from solutions with materials described in Example 22 (Table 9). Tensile testing was carried out on an Instron Universal Testing Machine. The results are summarised in Table 11.

The results indicate that the polyurethaneureas prepared from PHMO linked with MDI and IPDI were significantly high in tensile and tear strength compared to that prepared from unlinked PHMO.

TABLE 11

Tensile properties of polyurethaneurea series

| Polyurethane | Elongation at break (%) | Ultimate tensile stress (MPa) | Young's modulus (MPa) | Tear strength (N/mm) |
|---|---|---|---|---|
| PU-C | 688 ± 47 | 16 ± 0.9 | 8 ± 0.7 | 32 ± 1.5 |
| PU-1 | 646 ± 24 | 31 ± 2.4 | 18 ± 0.7 | 64 ± 2.3 |
| PU-2 | 607 ± 6 | 16 ± 0.5 | 10 ± 0.3 | 65 ± 4.0 |
| PU-3 | 527 ± 51 | 12 ± 1.3 | 11 ± 0.7 | 38 ± 4.0 |
| PU-4 | 582 ± 35 | 15 ± 0.7 | 13 ± 0.6 | 52 ± 8.3 |
| PU-5 | 681 ± 47 | 35 ± 3.0 | 20 ± 1.3 | 61 ± 11.5 |
| PU-6 | 453 ± 38 | 13 ± 1.1 | 14 ± 0.6 | 37 ± 2.7 |

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A thermoplastic polyurethane or polyurethaneurea elastomer material made by a process comprising the steps:
    (a) forming a reaction product of
      a linked macrodiol;
      a diisocyanate; and
      a polyol; wherein the diisocyanate is in molar excess relative to the linked macrodiol and the polyol; and
    (b) further reacting the reaction product of step (a) with one or more chain extenders,
    wherein
    (i) the linked macrodiol is

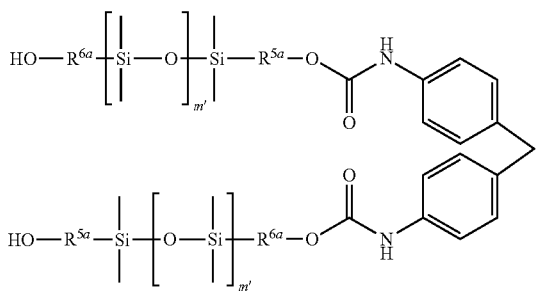

and the polyol is

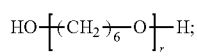

or
(ii) the linked macrodiol is

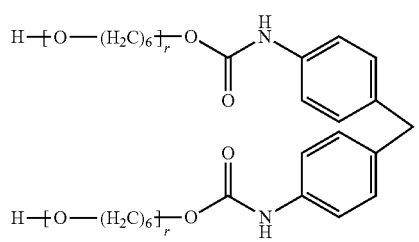

and the polyol is

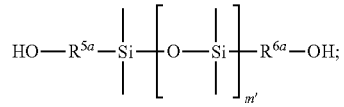

or
(iii) the linked macrodiol is

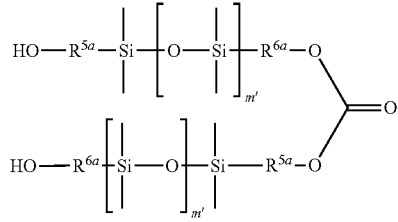

and the polyol is

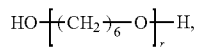

wherein, independently for each occurrence,
  $R^{5a}$ and $R^{6a}$ are each independently selected from a straight chain, branched or cyclic, saturated and unsaturated hydrocarbon radical optionally interrupted with one or more heteroatoms independently selected from O, N and S;
  m' is an integer of 1 to 50; and
  r is an integer of 2 to 50.

2. The thermoplastic polyurethane or polyurethaneurea elastomer material of claim 1, wherein
the linked macrodiol is

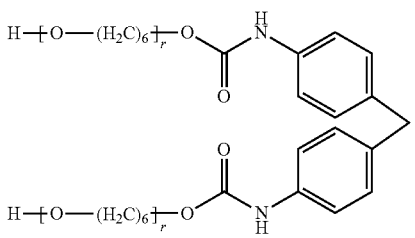

and the polyol is

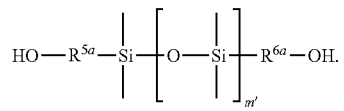

3. The thermoplastic polyurethane or polyurethaneurea elastomer material of claim 1, wherein $R^{5a}$ and $R^{6a}$ are independently selected from optionally substituted alkyl or alkoxyalkyl groups.

4. The thermoplastic polyurethane or polyurethaneurea elastomer material of claim 3, wherein $R^{5a}$ and $R^{6a}$ are independently selected from optionally substituted propylene, butylene, pentylene, hexylene, ethoxypropyl, propoxypropyl and butoxypropyl groups.

5. The thermoplastic polyurethane or polyurethaneurea elastomer material of claim 1, wherein $R^{5a}$ and $R^{6a}$ are $(CH_2)_2O(CH_2)_3$.

6. The thermoplastic polyurethane or polyurethaneurea elastomer material of claim 1, wherein the chain extenders are selected from diol and diamine chain extenders.

7. The thermoplastic polyurethane or polyurethaneurea elastomer material of claim 6, wherein the chain extenders comprise 1,2-ethylenediamine.

8. The thermoplastic polyurethane or polyurethaneurea elastomer material of claim 6, wherein the chain extenders comprise 1,3-bis-(4-hydroxybutyl)-1,1,3,3-tetramethyldisiloxane.

9. The thermoplastic polyurethane or polyurethaneurea elastomer material of claim 1, wherein the thermoplastic polyurethane or polyurethaneurea elastomer material further comprises one or more diisocyanate residues.

10. The thermoplastic polyurethane or polyurethaneurea elastomer material of claim 9, wherein the diisocyanate is 4,4'-methylenediphenyl diisocyanate (MDI).

11. The thermoplastic polyurethane or polyurethaneurea elastomer material of claim 1, wherein the thermoplastic polyurethane or polyurethaneurea elastomer material has a tensile strength ≥20 MPa at about 23° C.

12. The thermoplastic polyurethane or polyurethaneurea elastomer material of claim 1, wherein the thermoplastic polyurethane or polyurethaneurea elastomer material has an elongation at break of ≥500% at about 23° C.

13. The thermoplastic polyurethane or polyurethaneurea elastomer material of claim 1, wherein the thermoplastic polyurethane or polyurethaneurea elastomer material has a Young's modulus of ≥15 MPa at about 23° C.

14. The thermoplastic polyurethane or polyurethaneurea elastomer material of claim 1, wherein the thermoplastic polyurethane or polyurethaneurea elastomer material has a polydispersity index (PDI) of ≤3.00.

15. An article which is composed wholly or partly of the polyurethane or polyurethaneurea elastomer material made by a process comprising the steps:
(a) forming a reaction product of
a linked macrodiol;
a diisocyanate; and
a polyol; wherein the diisocyanate is in molar excess relative to the linked macrodiol and the polyol; and
(b) further reacting the reaction product of step (a) with one or more chain extenders, wherein
(i) the linked macrodiol is

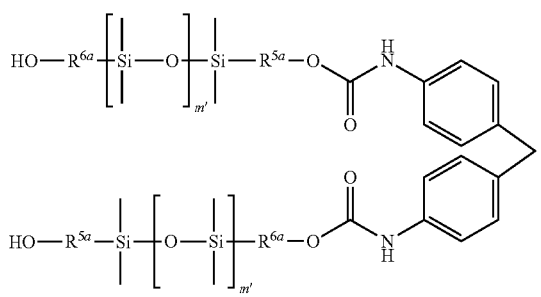

and the polyol is

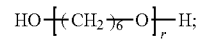

or
(ii) the linked macrodiol is

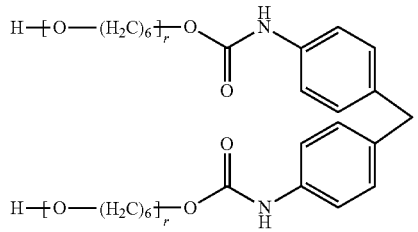

and the polyol is

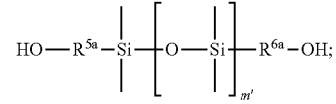

or
(iii) the linked macrodiol is

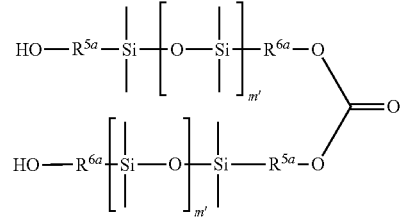

and the polyol is

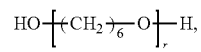

wherein, independently for each occurrence,
$R^{5a}$ and $R^{6a}$ are each independently selected from a straight chain, branched or cyclic, saturated and unsaturated hydrocarbon radical optionally interrupted with one or more heteroatoms independently selected from O, N and S;
m' is an integer of 1 to 50; and
r is an integer of 2 to 50.

16. The article of claim 15, wherein the article is selected from artificial leather, shoe soles, cable sheathing, varnishes, coatings, structural components for pumps or vehicles, mining ore screens, conveyor belts, laminating compounds, fibres, textiles, separation membranes, sealants, adhesive components, and a medical device.

17. The article of claim 16, wherein the article is a medical device selected from an implant, a cardiac pacemaker, defibrillator, catheter, heart valve, cardiac assist device, vascular graft, an implantable prosthesis, a cannula, extracorporeal device, artificial organ, pacemaker lead, defibrillator lead, blood pump, balloon pump, A-V shunt, biosensor, membrane for cell encapsulation, drug delivery device, wound dressing, artificial joint, orthopaedic implant, and a soft tissue replacement.

18. The article of claim 17, wherein the article is a heart valve; and the heart valve comprises a plurality of valve leaflets; and a support structure, wherein one or more of the valve leaflets are composed wholly or partly of the polyurethane or polyurethaneurea elastomer material.

19. The article of claim 18, wherein the article is an aortic, mitral, or tricuspid valve.

20. The article of claim 18, wherein the article is a pulmonary valve.

* * * * *